(12) United States Patent
Sideris

(10) Patent No.: US 8,262,884 B2
(45) Date of Patent: Sep. 11, 2012

(54) ELECTROPHORESIS DEVICE AND METHOD FOR SEPARATING OBJECTS

(75) Inventor: Dimitrios Sideris, Richmond (GB)

(73) Assignee: Genetic Microdevices Limited (GB)

( * ) Notice: Subject to any disclaimer, the term of this patent is extended or adjusted under 35 U.S.C. 154(b) by 1122 days.

(21) Appl. No.: 11/813,191

(22) PCT Filed: Dec. 22, 2005

(86) PCT No.: PCT/GB2005/004992
§ 371 (c)(1),
(2), (4) Date: Oct. 22, 2007

(87) PCT Pub. No.: WO2006/070176
PCT Pub. Date: Jul. 6, 2006

(65) Prior Publication Data
US 2008/0083621 A1    Apr. 10, 2008

(30) Foreign Application Priority Data
Dec. 31, 2004 (GB) .................................. 0428548.2

(51) Int. Cl.
G01N 27/447 (2006.01)
G01N 27/453 (2006.01)
B01D 57/02 (2006.01)

(52) U.S. Cl. ....................... 204/547; 204/643

(58) Field of Classification Search .................. 204/601, 204/645, 547, 451, 643
See application file for complete search history.

(56) References Cited

U.S. PATENT DOCUMENTS

| | | | |
|---|---|---|---|
| 512,602 A | 6/1992 | Soane et al. | |
| 6,277,258 B1 | 8/2001 | Ivory et al. | |
| 6,770,182 B1 * | 8/2004 | Griffiths et al. | 204/453 |
| 2002/0043462 A1 | 4/2002 | Ivory et al. | |

FOREIGN PATENT DOCUMENTS

| | | |
|---|---|---|
| DE | 101 36 275 | 12/2002 |
| EP | 0 708 330 | 4/1996 |
| WO | WO 03/051520 | 6/2003 |

OTHER PUBLICATIONS

International Preliminary Report on Patentability dated Jun. 6, 2007 for PCT/GB2005/004992.
International Search Report mailed Mar. 6, 2006 for PCT/GB2005/004992.
Cyclic electrophoretic and chromatographic separation methods, Electrophoresis 2004, 25, 243-252, Jan. C. T. Eijkel et al.
An AC electroosmotic micropump for circular chromatographic applications, S. Debesset et al., The Royal Society of Chemistry 2004, Lab Chip, 2004, pp. 396-400.

* cited by examiner

*Primary Examiner* — J. Christopher Ball
(74) *Attorney, Agent, or Firm* — James P. Muraff; Neal, Gerber & Eisenberg LLP

(57) ABSTRACT

An electrophoresis method is provided for separating objects in a fluid contained in a separation channel. The method comprises: applying an electric field along the separation channel, the electric field having a field profile, and thereby causing at least some of the objects to move relative to the fluid; varying the applied electric field so as to adjust the field profile relative to the separation channel, thereby causing the objects to separate into bands under the combined influences of an electric force due to the electric field and a hydrodynamic force due to the fluid.

54 Claims, 23 Drawing Sheets

Figure 10
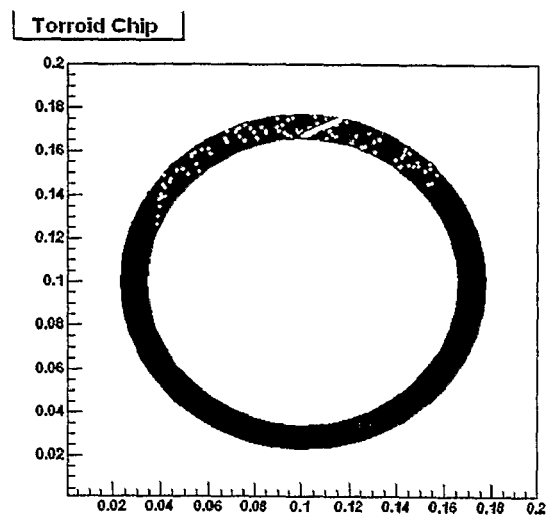
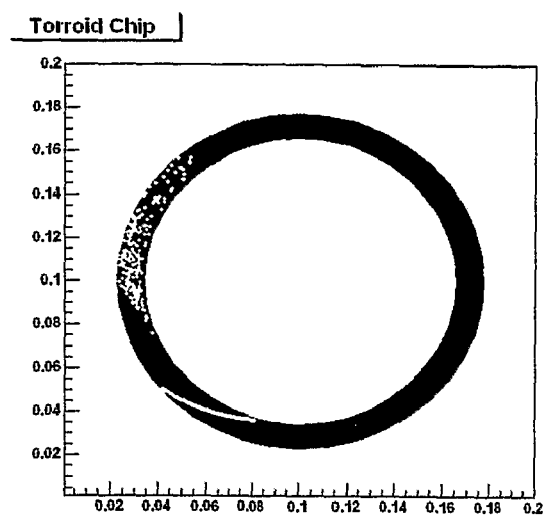
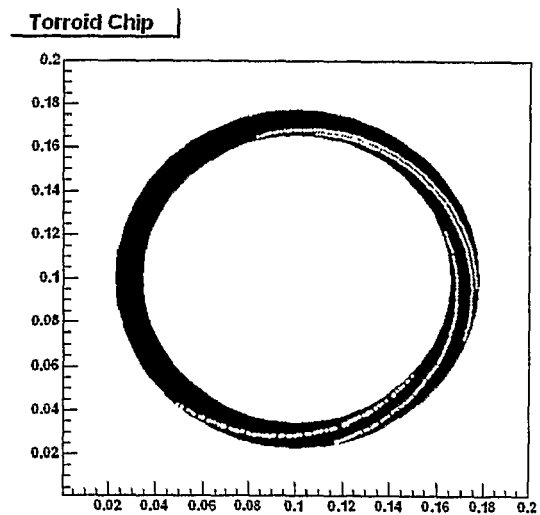

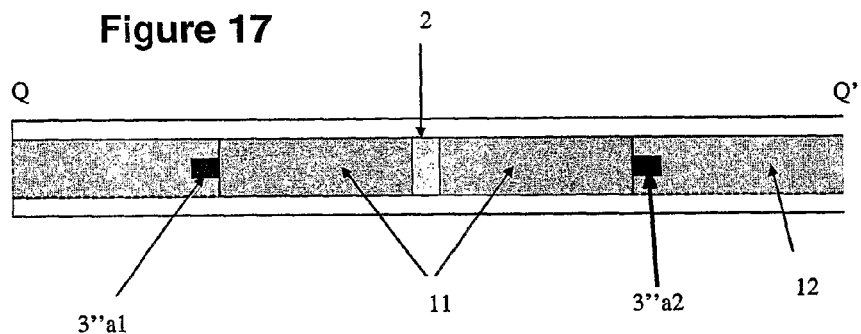
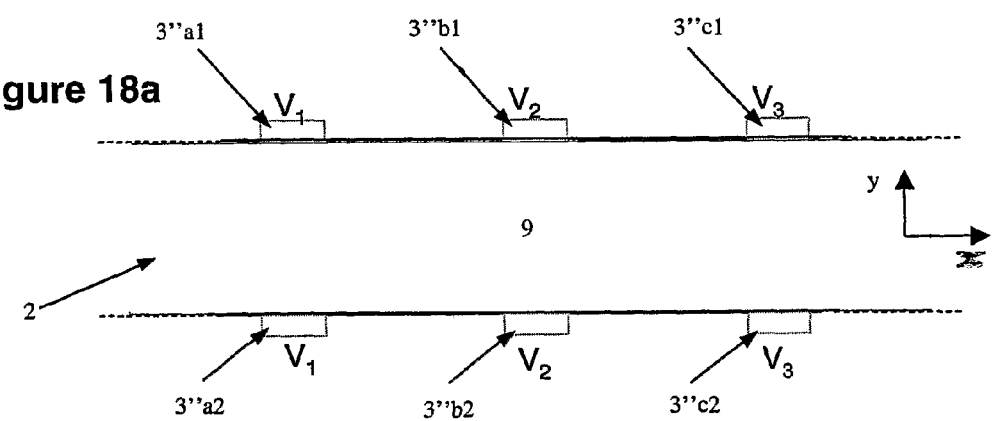
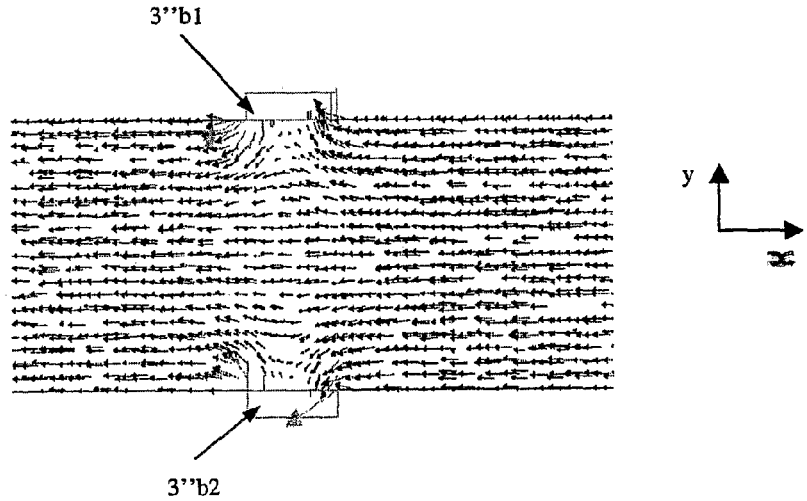

ELECTROPHORESIS DEVICE AND METHOD FOR SEPARATING OBJECTS

CROSS REFERENCE TO RELATED APPLICATIONS

This application is a U.S. national-stage filing from PCT International Application No. PCT/GB2005/004992, filed 22 Dec. 2005, which claims priority from U.K. Patent Application No. 0428548.2, filed 31 Dec. 2004, the contents of which are both incorporated herein by reference.

FIELD OF THE INVENTION

This invention relates to a method and device for carrying out electrophoretic separation of objects in a fluid. The technique described eliminates band diffusion and achieves fast, high resolution separation.

BACKGROUND

Electrophoresis refers to the motion of charged objects through a fluid under the influence of an electric field. This phenomenon can be used to separate objects according to their electric and hydrodynamic properties, and a number of techniques for exploiting this are in widespread use. The objects to be separated, commonly proteins or other biomolecules, are typically suspended in a fluid such as a buffer solution or a gel. A small section of the solution containing the objects is placed at the beginning of a separation channel containing a fluid or gel and subsequently a constant electric field is generated along the channel. Under the influence of this field the said objects start moving towards the opposite end of the channel. As they migrate through the fluid, they experience differential hydrodynamic force depending on their shape and size. Due to this different hydrodynamic force applied to them, the objects move with different terminal velocity depending on their individual characteristics and thus they separate and form "bands". Due to their different terminal velocities, the distance between the bands increases with time.

A band is essentially a group of objects having like electrical and hydrodynamic properties. One of the key disadvantages of electrophoresis is the fact that the bands, as they move at their terminal velocity, undergo thermal diffusion. This makes the bands broaden with time reducing the resolution of the separation.

Various known implementations of electrophoresis are reviewed in "Cyclic electrophoretic and chromatographic separation methods", Eijkel et al, Electrophoresis 2004, 25, 243-252.

There are also a number of variants to the conventional electrophoresis method that attempt to limit the thermal diffusion.

One such method is Iso-Electric-Focussing (IEF) which deploys a pH gradient in the separation channel. As the objects move through the fluid under the influence of a constant electric field, their apparent charge changes due to the changing pH along the channel. Each object, depending on its charge characteristics, moves until a point where its apparent charge is zero. This is called the "isoelectric point". At that point the object stops moving as it reaches an equilibrium position. Each object with different charge characteristics stops at a different point along the channel and thus a separation of the objects takes place. The bands of objects can then be detected and investigated, for example by imaging.

The advantage of this method is the elimination of thermal diffusion and the disadvantage is the limited accuracy of the pH gradient. Another disadvantage is the increased separation times (typically many hours).

Another electrophoresis variant is disclosed in US-A-2002/0043462. Particles are separated by applying a first force resulting from buffer flow through the chamber which is opposed by an electric field gradient. The shape of the static electric field is such that the particles separate into bands along the chamber. The bands represent equilibrium positions at which the net force on each molecule is zero. Once the bands are formed, the applied electric field may be modified so as to manipulate the bands, for example moving a band of interest to an exit point. However as in the case of other known systems, the device relies on a constant flow of buffer through the chamber in order to impose the appropriate hydrodynamic force on each particle and thus achieve successful separation. This leads to a number of problems.

Firstly, the pumping and monitoring equipment required to achieve the highly accurate liquid flow through the channel leads to a potentially expensive and complicated infrastructure. As a result, the systems are typically costly and can be unreliable, comprising a number of complex mechanical components. The accuracy of the buffer flow is essential to the accuracy and resolution of the device.

Secondly, a common problem associated with the use of flowing liquids, and experienced heavily in high performance liquid chromatography (HPLC) processes using pressure driven flow, is that the liquid interacts with the channel walls. As a result, the liquid does not flow with a constant velocity across the channel cross-section but rather moves more slowly adjacent to the walls and faster towards the middle of the channel. This creates a parabolic velocity front, which directly affects the band shape of the separated molecules. The greater the departure from a constant velocity front, the wider the bands become, thus reducing resolution in the device. The separation process can be sped up by increasing the buffer flow rate. This is because the time taken for molecules to reach their equilibrium position shortens and hence the separation should complete more quickly. In a first approach, increasing the flow rate should also narrow the stationary bands because the exerted hydrodynamic and electric forces are larger. This would result in improved resolution.

However, as the flow rate is increased, the parabolic flow profile becomes accentuated, tending to cancel out the expected improvement in resolution.

Conventional electrophoresis often involves the use of gels as the separation fluid. The relatively high viscosity reduces diffusion and so improves resolution. However, it is difficult, if not impossible, to use gels with techniques requiring buffer flow (such as the two aforementioned methods) because the gels do not generally flow easily.

What is needed is a technique that effectively controls thermal diffusion and which eliminates the need for a constant flow of separation fluid through the apparatus. Such a method should achieve fast separation and high resolution. The present invention is provided to solve the problems discussed above and other problems, and to provide advantages and aspects not provided by prior electrophoresis methods and systems. A full discussion of the features and advantages of the present invention is deferred to the following summary, detailed description, and accompanying drawings.

SUMMARY OF THE INVENTION

In accordance with the present invention, an electrophoresis method for separating objects in a fluid contained in a separation channel comprises:

applying an electric field along the separation channel, the electric field having a field profile, and thereby causing at least some of the objects to move relative to the fluid;

varying the applied electric field so as to adjust the field profile relative to the separation channel, thereby causing the objects to separate into bands under the combined influences of an electric force due to the electric field and a hydrodynamic force due to the fluid.

Further in accordance with the present invention, an electrophoresis device for separating objects comprises:

a separation channel which, in use, contains a fluid and the objects to be separated;

means for applying an electric field along the separation channel, the electric field having a field profile, whereby objects in the separation channel are caused to move relative to the fluid;

a controller adapted in use to apply and vary the applied electric field so as to adjust the electric field profile relative to the separation channel, whereby objects in the separation channel are caused to separate into bands under the combined influences of an electric force due to the electric field and a hydrodynamic force due to the fluid.

It will be appreciated that the term "fluid" is used here to describe any appropriate separation medium. For example, the fluid could be a liquid, a gel, a sieving matrix or any other material that can generate frictional or hydrodynamic forces on a moving object.

By varying the applied electric field relative to the separation channel from substantially the outset of the separation process (as opposed to after the bands are formed), the objects can be separated into bands without the need for fluid flow through the separation channel. The applied electric field establishes a time-varying field profile, which achieves electrophoretic separation by forcing the particles to move through the fluid, which can therefore be stationary itself. It should be noted that the electric field is non-constant (with respect to the channel) along at least a portion of the field profile. In other words a (non-zero) time-varying electric field gradient is applied. As a result, the objects separate into moving bands which do not widen with time.

This does away with the need for complicated and expensive pumping equipment and eliminates problems associated with the parabolic velocity front encountered in conventional systems. Further, the technique lends itself well to the use of a gel or sieving matrix as the separation fluid, since no fluid flow is required. The particular electric field and its variation will depend on the types of object to be separated and the fluid used as the separation medium. Preferably however, the electric field is varied in such a way that the field profile moves relative to the separation channel.

The field profile could change in shape and/or intensity as it moves, but further preferably, the field profile remains unchanged as it moves relative to the separation channel (i.e. maintains its shape and intensity). Typically, it is convenient for the bands to be separated along the channel and so it is preferable that the electric field is varied in such a way that the electric field profile translates along the separation channel.

Depending on the objects to be separated, it may be beneficial to maintain some degree of fluid flow through the channel. However, as already described it is usually advantageous if fluid flow can be eliminated and so it is preferable that the fluid and the separation channel are substantially stationary with respect to one another.

The particular shape of the applied electric field will be selected according to the desired output from the device. However typically the electric field profile is shaped such that the net force experienced by each object, resulting from the combination of the electric force exerted by the field and the hydrodynamic force exerted by the fluid, is such that the width of each separated band remains substantially constant with time. Preferably, the field profile is such that the bands acquire a finite width (typically along the separation channel), and diffusion of the objects in each band is bound or confined so that the band width does not change with time as long as the experimental conditions remain the same. Hereinafter this is referred to as "bound diffusion".

Once the objects are separated into bands, the electric field could be removed. However, it is advantageous to continue the application of the field and vary it such that, once the objects have separated into bands, each band moves with a non-zero terminal velocity relative to the separation channel. This maintains high resolution since the continuously moving bands do not diffuse over time.

In conventional electrophoretic separations, different bands move with different terminal velocities. In other words as they move through the buffer or gel, they get further and further apart from each other. Assuming that the increase in relative distance is faster than the band widening due to diffusion, the resolution of electrophoresis increases with larger separation lengths (ie. longer separation channels). However, the signals weaken with time due to the diffusion and very large separation channels are impractical. Therefore in practice "band loss" can occur when bands reach the end of the channel. In contrast, in the present invention, it is preferable that the bands move with substantially equal terminal velocity. Therefore the separation efficiency does not depend on the length of the separation channel but instead on the characteristics of the applied time varying electric field and the characteristics of the separation buffer. Preferably, the terminal velocity of each band is essentially the same and thus the spacing between each is maintained. Further preferably, the terminal velocity is constant over time.

Advantageously, the applied electric field is of the form $$E(x,t)=((x-kt)^n)$$

where x is a space coordinate, typically along the separation channel, t is a time coordinate, n and k are each real numbers and n is not zero. In other words, $E(x,t)$ can be any function of $x-kt$, including linear, exponential or a $n^{th}$ power polynomial. In addition, it is advantageous if at least a portion of the electric field is monotonic with respect to distance along the channel (x). This facilitates the separation of sample molecules and confinement of band diffusion.

Conveniently, the method further comprises the steps of mixing the objects to be separated with the fluid and placing the mixture in the separation channel. Alternatively, the fluid could be placed in the separation channel and then the sample inserted, the sample comprising at least objects to be separated. The sample could further comprise fluid, which may or may not be the same as the fluid already contained in the separation channel. These steps could take place prior to the application of the electric field or once the field is established. In some aspects of sample loading, the sample may be introduced into the channel while the field is on. This is especially useful for closed loop separations. For example, in DNA sequencing, four separate injections take place in a single separation experiment. Sequential injections can be useful in many applications and those would generally happen with the electric field switched on in advance.

Preferably, the method further comprises the step of detecting the bands. Typically, the bands are imaged. Imaging or detecting can take place after separation is complete or throughout the separation process. Indeed, useful conclusions may be derived from the "rising profiles" of the bands as a function of time. In particular, the rising profiles of bands in relation to sequential injections may be very useful in order to correlate those bands to a given injection, for example in DNA sequencing.

Advantageously, the method further comprises the step of modifying the electric field, after the objects have separated into bands, to adjust spacing between the bands, band positioning or band resolution. This can be achieved by changing the shape of the electric field profile, its intensity or its position along the separation channel, for example. This can be used to view a different range of bands, move a band to a particular point along the separation channel or adjust the number of bands that are resolvable, for example. In particular, the electric field may be modified by changes to its time-dependence and/or its intensity.

Some applications involve removing certain separated objects from the sample mixture. In such cases, it is preferable that the method further comprises the step of extracting a band of interest from the separation channel after the objects have separated.

Advantageously, the method further comprises the step of oscillating the electric field, causing the motion of the bands to reverse in direction, the bands thus moving back and forth along the separation channel. This allows each band to be imaged or otherwise detected repeatedly and thus can increase the sensitivity of the device for low concentration components. This can also be achieved by causing the bands to travel in circuits around a closed loop separation channel.

In other embodiments, the separation channel is a closed loop and in this case it is preferable that the applied electric field is periodic around the loop. In all of the embodiments, the means for applying the electric field could comprise any known field shaping apparatus, for example a variable resistance along the channel. Preferably however the means for applying an electric field comprise a plurality of electrodes spaced along the separation channel. This technique allows accurate and intricate shaping of the electric field and is conveniently controlled by varying the voltage applied to each electrode individually. It is preferable that the electrodes are spaced from the interior of the separation channel such that current is not conducted between the electrodes and the fluid. This avoids current flow through the separation fluid and thus prevents excessive joule heating which can lead to erratic behaviour in the system. Conveniently, the electrodes comprise conductive ink printed on or adjacent to the separation channel.

Advantageously, at least some of the plurality of electrodes are spaced from the interior of the separation channel by a layer of electrically resistive material. In this way, the electric field established inside the channel is smoother, less distorted by the local effects of the electrodes. The resistive material is preferably a semiconductor or doped semiconductor, most preferably doped silicon.

Preferably, the separation channel is a capillary. Such dimensions allow the electric field to be accurately controlled across the channel cross-section and lead to well defined bands even with low concentration samples. In one preferred embodiment the separation channel is rectilinear. Alternatively, the separation channel could be in the form of a closed loop. This could be substantially circular or, preferably, have linear sections.

Conveniently, the separation channel is engraved in a substrate such as a glass plate. This provides a convenient way of implementing the device on a very small scale. Preferably, the device is a microfluidic device.

Advantageously, the device comprises a plurality of separation channels, each separation channel being provided with means for applying the electric field and a controller. The electric field applied to each separation channel could be chosen individually according to the objects to be separated in each channel. Preferably however the electric field applied to each separation channel is the same. Conveniently, the electric field applied to each separation channel is controlled by the same controller. Preferably, the objects to be separated comprise biomolecules, proteins, polymers, DNA, RNA or biological cells.

BRIEF DESCRIPTION OF THE DRAWINGS

At least one example of an electrophoresis device and method in accordance with the present invention will now be described with reference to the following figures.

FIGS. 3a and 3b are graphs illustrating forces to which a particle is subjected;

FIG. 10 illustrates band separation in a curved channel without velocity correction;

FIG. 17 is a cross-sectional view of the example configuration shown in FIG. 16, taken along the line Q-Q;

FIG. 18A schematically depicts a portion of a fifth exemplary electrode configuration in plan view;

FIG. 18B shows the electric field lines calculated for the fifth electrode configuration;

DETAILED DESCRIPTION

Figure 1:
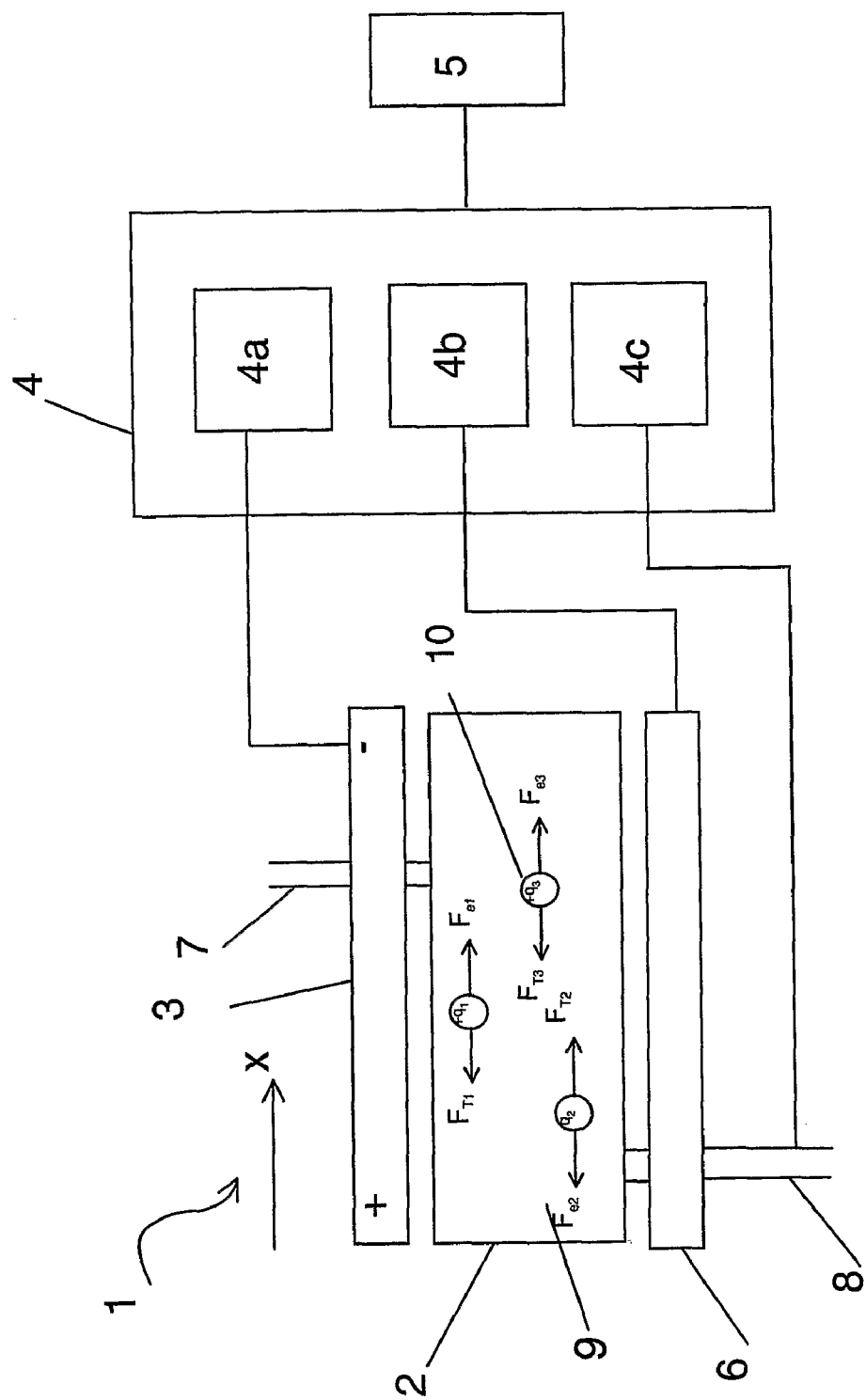
FIG. 1 is a schematic representation of an electrophoretic device.

The invention will now be described with reference to exemplary embodiments which are provided to assist in an understanding of the teaching of the invention, but it will be understood that the invention is not to be construed as being limited in any fashion to these exemplary embodiments.

The electrophoretic device 1 comprises a separation channel 2, which could be implemented in a capillary or microfluidic chip for example, means 3 for applying an electric field along the separation channel 2 and a controller 4 for controlling at least the electric field. The separation channel 2 contains a fluid 9 which may be a buffer of choice or a gel, for example. The objects 10 to be separated are suspended within the fluid 9 in the separation channel 2. The device 1 may further be provided with a detector 6, which may communicate with the controller 4, and input and output ports 7 and 8 respectively, which may also be controlled by the controller 4. The controller 4 in turn generates an output 5.

As will be described in more detail below, the separation channel 2 could take any shape including linear or curved. In some embodiments, the separation channel can form a closed loop. The electric field applying means 3 could comprise field shaping electrodes or a variable resistance along the channel 2, for example. The objects to be separated generally include at least some charged bodies, and typically comprise polymers such as proteins, DNA molecules or RNA molecules or other types of biomolecules such as biological cells. The particular separation fluid 9 selected will depend on the objects 10 to be separated. For example, the fluid could be a liquid or gas, such as a buffer. Alternatively, the fluid could be a gel or other sieving matrix. The latter is a material which may have pores through which the separating objects have to pass as they are moving. This results in the application of frictional force that is a function of the shape/size of the object. The frictional force is similar to, but not the same as, hydrodynamic force as it obeys different laws. Indeed, any fluid, gel matrix or other sieving material that can generate frictional or hydrodynamic forces on a migrating object (e.g. a macromolecule) could be selected. Advantageously, a gel may be employed as the separation medium, which reduces unwanted diffusion of the separated objects still further owing to its increased viscosity. This is generally not possible in conventional systems which require constant fluid flow.

In operation, an electric field E is applied by the field shaping means 3 along the separation channel 2. The controller 4 includes a module 4a which controls the electric field applying means 3 so as to induce a time varying electric field on the separation channel 2 and its contents. The electric field exerts a force Fe on each object 10 which is proportional to its charge q. This causes the object 10 to move relative to the fluid 9 which induces a hydrodynamic (frictional) force $F_T$ on the object. For example, three such objects and the forces on each are shown schematically in FIG. 1.

The time variation of the electric field is calculated so as to force the objects 10 in the separation channel 2 to start moving and converge into bands moving along the separation channel 2 and not diffusing (widening). The moving bands can be imaged, or otherwise detected, by a detector 6 which communicates with another control module 4b. If desired, selected bands of interest can be extracted from the separation channel 2 by means of an exit port 8, also controlled by a module 4c of controller 4.

The particular shape and characteristics of the electric field will be selected according to the type of objects 10 to be separated and the properties of the separation fluid 9. However, in all cases, the electric field will have a field profile. In other words, the electric field value varies along at least a portion of the length of the separation channel, i.e. a time-varying electric field gradient is employed. Typically, a time varying electric field E is applied to the channel 2, of the form:

$$E(x,t)=E((x-kt)^n), n\in \Re \text{ and } n\neq 0, k\in \Re \quad (1.1)$$

where x is the space coordinate (typically the distance along the separation channel 2), t is the time and n and k are constant real numbers ($\Re$).

Figure 2A:
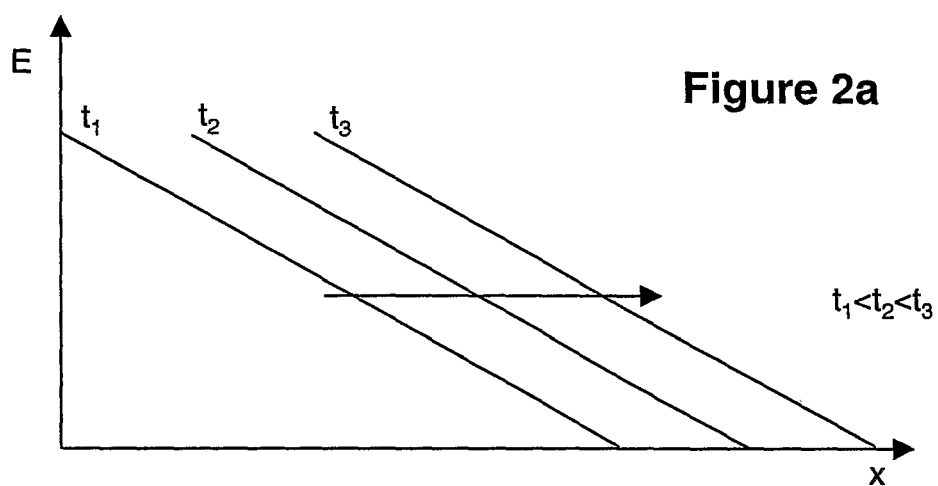
FIGS. 2a, b and c are graphs depicting exemplary electric field profiles and their variation with time.
Figure 2B:
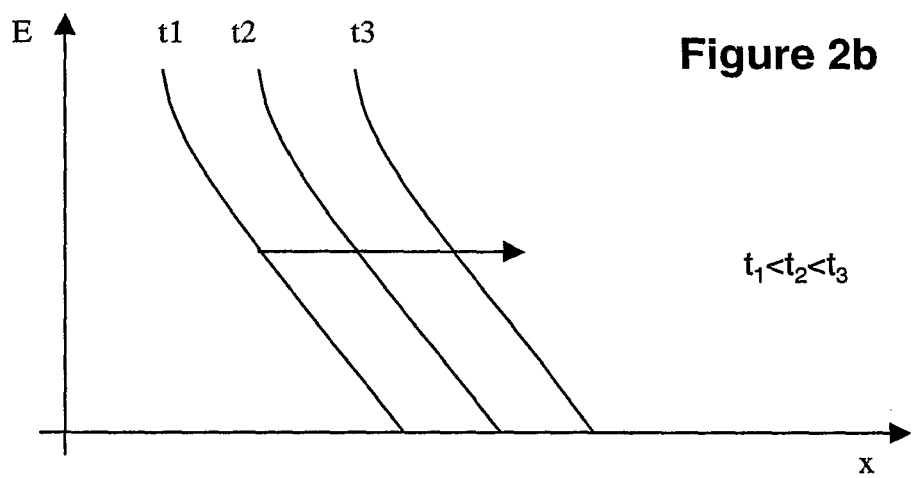
Figure 2C:
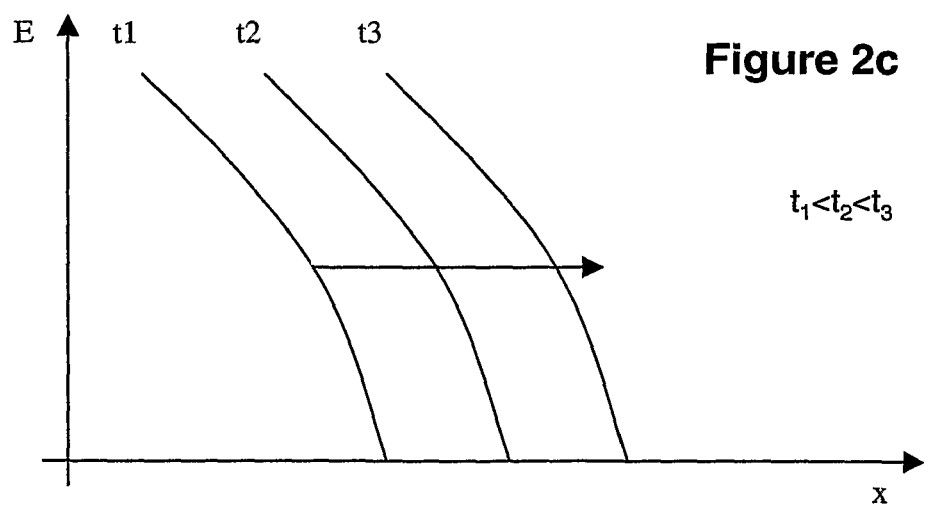

It will be understood that the electric field could be linear or non-linear, for example exponential or an $n^{th}$ power polynomial. Schematic examples of linear and non-linear field profiles are shown in FIGS. 2a, 2b and 2c. It is preferable that at least a portion of the field profile is monotonic, that is, its first derivative (with respect to distance along the channel) does not change sign. This facilitates separation of sample molecules and confinement of band diffusion. Preferably, the monotonic section should have the correct sign in relation to the parameter k. Further preferably, the electric field should be continuous along at least a portion of the field profile, i.e. there are no sudden jumps in the field. It should further be noted that the field profile can move in either direction (+x or −x) along the separation channel.

For the sake of example we will examine the simplest case of a linear field profile where n=1 (a and c are introduced as constants):

$$E(x,t)=a(x-kt+c), a\in \Re, c\in \Re \quad (1.2)$$

This field shape is depicted schematically in FIG. 2a for a series of increasing times $t_1$, $t_2$ and $t_3$. Note the field profile effectively moves along the x-axis.

For a particle or object 10 with charge q, the electric force $F_e$, is:

$$F_e(x,t)=qE(x,t) \quad (1.3)$$

Figure 3A:
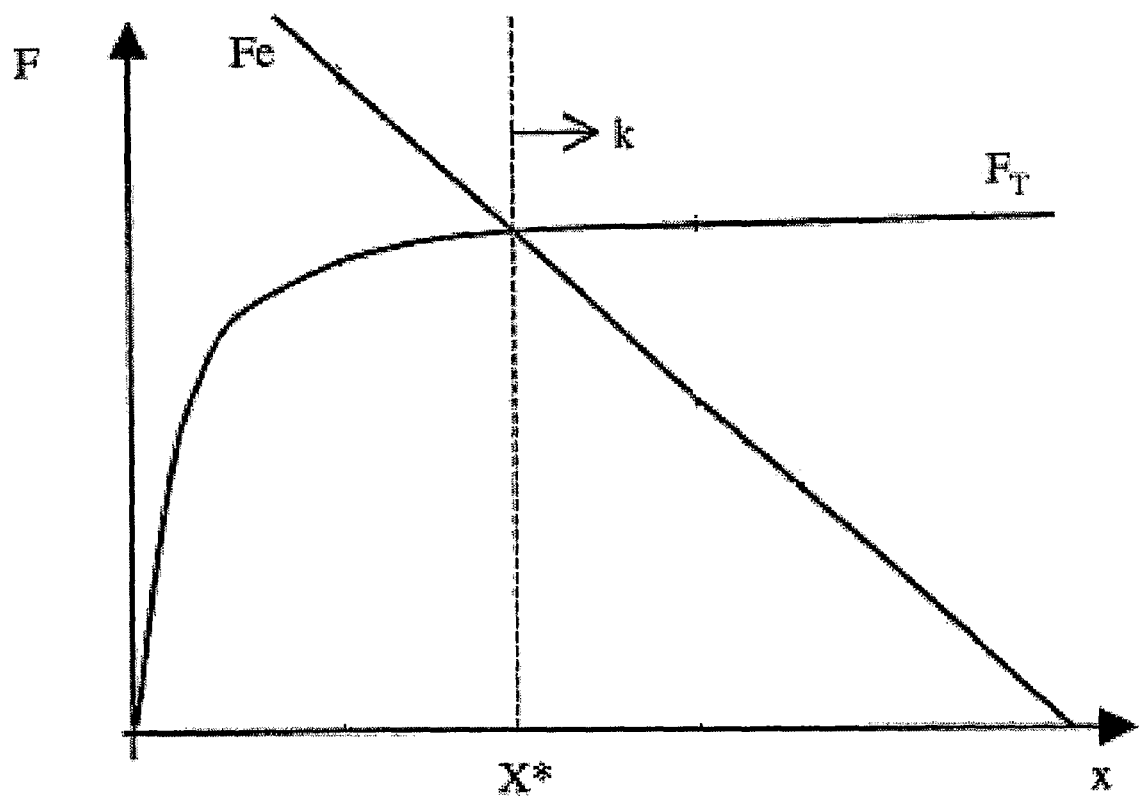
Figure 2B:
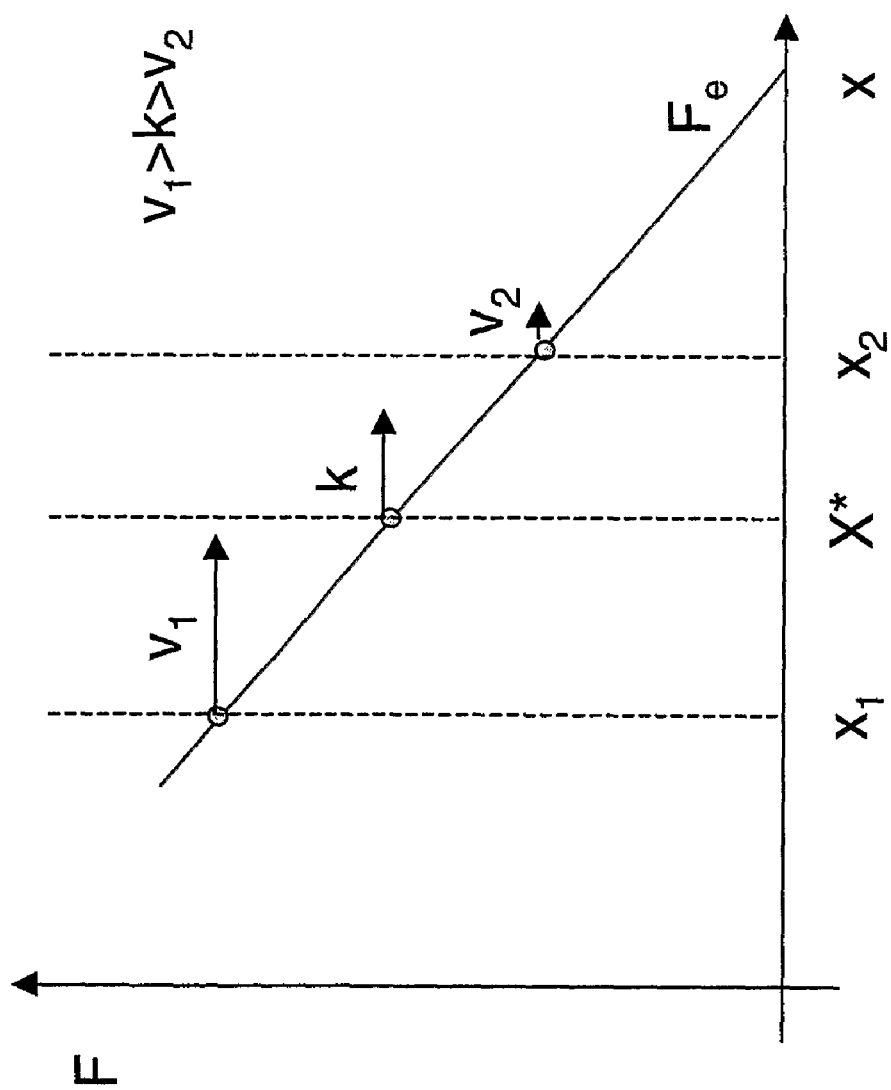

In the current invention the particle 10 will move within fluid 9 and therefore there will be a frictional (hydrodynamic) force $F_T$, opposing its motion. This force in the general simplified case will be of the form:

$$F_T(x,t)=fv(x,t), f>0 \text{ and } f\in \Re \quad (1.4)$$

where v(x,t) is the velocity of the particle 10 and f is a coefficient describing the intensity of the friction and which depends on the shape and size of the particle 10. When subjected to these two forces, each object 10 will attempt to migrate to its equilibrium (lowest energy) position, at which $F_e-F_T=0$. This is identified as X* in FIG. 3a, and it moves with velocity k. For example, suppose two identical particles start at positions $x_1$ and $x_2$ (FIG. 3b). At $x_1$, the electric force is greater than the electric force at X*, which in turn is greater than the electric force at $x_2$. This results in sorted velocities which are $v_1 > k > v_2$.

Therefore the object that started at x1 moves faster than k and catches up with the moving point X* (which moves with velocity k). As the object is catching up with X* it moves relatively to the electric force profile towards lower values and therefore it decelerates until it reaches velocity k. Then its relative position to the force profile stays constant and therefore it moves with constant terminal velocity k from then on.

FIG. 3b shows how two identical particles will acquire sorted velocities in order to finally comigrate with velocity k.

The aim now is to calculate the velocity v(x,t) (relative to the separation channel). For a given set of initial conditions of the particle 10, only one coordinate is independent, say t. Therefore we need to calculate v(t) and x (t). The acceleration of the object 10 depends on the net force resulting from the combined influences of the electric force and the frictional force, which typically oppose one another (see FIG. 1). This gives:

$$m \frac{dv(t)}{dt} = F_e(x, t) - F_T(x, t) \quad (1.5)$$

where m is the mass of the particle 10. By substitution, the above becomes:

$$m \frac{dv(t)}{dt} = q\alpha(x - kt + c) - fv(t) \quad (1.6)$$

By differentiating the above equation for t (and changing the notation) we get:

$$mv''(t) = q\alpha[x'(t) - k] - fv'(t) \quad (1.7)$$

where x' (t)=v(t). Thus the above becomes a second order linear differential equation:

$$mv''(t) + fv'(t) - q\alpha v(t) + q\alpha k = 0$$

which has the following solution:

$$v(t) = k + Ae^{\frac{(-f + \sqrt{f^2 + 4q\alpha m})t}{2m}} + Be^{\frac{(f + \sqrt{f^2 + 4q\alpha m})t}{2m}} \quad (1.9)$$

where A and B are constants depending on the initial conditions. The first term can be potentially divergent for $t \to \infty$. However if the following condition is satisfied:

$$-f + \sqrt{f^2 + 4q\alpha m} < 0 \Rightarrow f^2 + 4q\alpha m < f^2 \Rightarrow q\alpha < 0 \quad (1.10)$$

the left term of (1.9) vanishes for $t \to \infty$.

For t=0 we can choose the velocity to be $v_o$:

$$v(0) = v_0 \therefore k + A + B = v_0 \Rightarrow B = v_0 - k - A \quad (1.11)$$

We need a further initial condition to determine A. By differentiating eq. (1.9) for t=0 we get:

$$v'(0) = \frac{A(-f + \sqrt{f^2 + 4q\alpha m})}{2m} - \frac{B(-f + \sqrt{f^2 + 4q\alpha m})}{2m} \quad (1.12)$$

For t=0 by definition $x = x_0$ and eq. (1.6) gives:

$$v'(0) = \frac{q\alpha x_0 + q\alpha c - v_0 f}{m} \quad (1.13)$$

By equating (1.12) and (1.13) we can solve for A:

$$A = \frac{Bf + 2c\alpha q + B\sqrt{f^2 + 4\alpha mq} - 2fv_0 + 2\alpha qx_0}{-f + \sqrt{f^2 + 4\alpha mq}} \quad (1.14)$$

Substituting into eq. (1.11) we get the final solution for B:

$$B = \frac{-2c - fk + k\sqrt{f^2 + 4\alpha mq} - 2fv_0 + 2kx_0}{2\sqrt{f^2 + 4\alpha mq}} \quad (1.15)$$

Now we have calculated both parameters A and B in terms of the initial conditions {t=0, $x = x_0$ & $v = v_0$} and thus we now know the velocity v(t) from eq. (1.9). Assuming that condition (1.10) holds, we see that:

$$\lim_{t \to \infty} v(t) = k \quad (1.16)$$

therefore the velocity of the particle 10 converges to a terminal velocity that is equal to the field parameter k. In addition, from eq. (1.16) we observe that the velocity will converge to k regardless of the values of f, a, q and m. In other words all particles of all shapes, sizes and electric charge (provided the charge sign is correctly aligned to the electric field as required by condition (1.10)) will converge to the same terminal velocity k.

Figure 4:
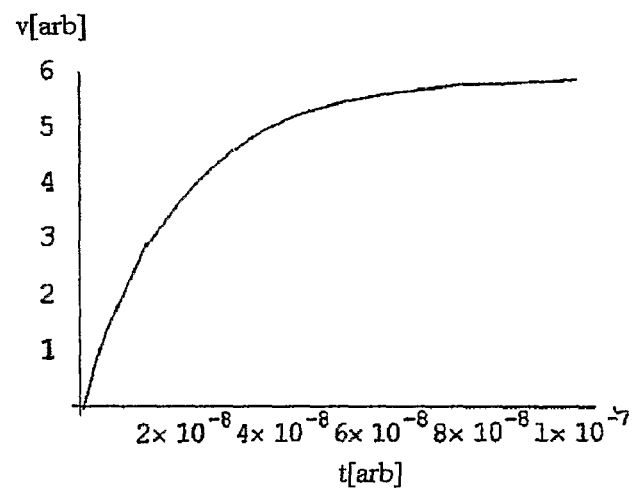
FIG. 4 shows the convergence of velocity with time of an exemplary molecule undergoing separation.

FIG. 4 shows the application of the equations of motion to a molecule with arbitrary characteristics. The velocity converges to a plateau, which is the terminal velocity.

In order to differentiate between bands, particles with different shape and charge characteristics must be physically separated from each other and form distinguished bands. Conveniently, all the objects 10 (and therefore the bands) should reach the same terminal velocity, which should be constant. If all of the particles 10 reached the same terminal velocity and comigrated in a superimposed fashion then the device would not be effective. The spatial position of a particle 10 is:

$$dx = v(t)dt \quad (1.17)$$

Substituting eq. (1.9) to the above and integrating we get:

$$\int_{x_0}^{x} dx = \int_{0}^{t} \left( k + Ae^{\frac{(-f + \sqrt{f^2 + 4q\alpha m})t}{2m}} + Be^{\frac{(f + \sqrt{f^2 + 4q\alpha m})t}{2m}} \right) dt \quad (1.18)$$

and thus:

$$x(t) = x_0 + \frac{2Am\left(-1 + e^{\frac{(-f + \sqrt{f^2 + q\alpha m})t}{2m}}\right)}{-f + \sqrt{f^2 + 4q\alpha m}} + \quad (1.19)$$

$$\frac{2Bm\left(1 - e^{-\left(\frac{f+\sqrt{f^2+4q\alpha m}}{2m}\right)t}\right)}{f + \sqrt{f^2+4q\alpha m}} + kt$$

Once the particle 10 has reached terminal velocity, the exponential terms are very small, and eq. (1.19) becomes:

$$x(t) = x_o + \frac{-2Am}{-f + \sqrt{f^2+4q\alpha m}} + \frac{2Bm}{f + \sqrt{f^2+4q\alpha m}} + kt. \quad (1.20)$$

This means that each particle 10 will move a distance determined by its terminal velocity plus a fixed amount which will depend on the charge, mass and friction characteristics of the particle. Therefore different particles will migrate with the same velocity but at a fixed distance from each other.

Identical particles even comigrate if their origin $x_0$ is different. This may be demonstrated by considering two identical particles that start from at two different positions $x_1$, $x_2$. By subtracting eq. (1.20) for both particles we get:

$$x_1(t,m,q,f,x_1) - x_2(t,m,q,f,x_2) = 0, t \to +\infty \quad (1.21)$$

Figure 5:
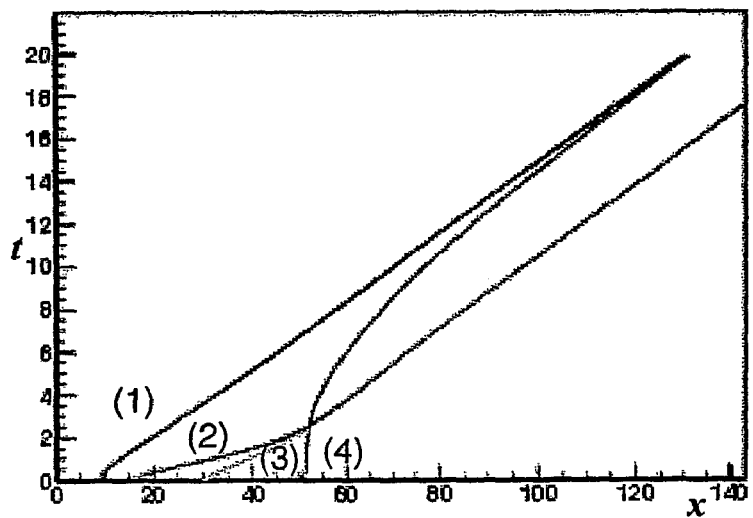
FIG. 5 is a graph illustrating the co-migration of identical particles.

Therefore identical particles will comigrate even if they started at a different origin along the separation channel. FIG. 5 demonstrates this using two pairs of identical particles. Particles (1) and (4) share like electrical and hydrodynamic characteristics, as do objects (2) and (3). Each particle in the pair starts at a different position along the x-axis. By applying an appropriate time varying field, the particles follow trajectories that make identical particles comigrate. The different pairs move with the same velocity but at a distance from each other. By controlling the field parameter k and the intensity a, the resolution (i.e. the band width and/or spacing along the x-axis) of the device can be adjusted. Also the dynamic range (the range of charge, mass and friction characteristics which will be resolved) of the device can be adjusted for a given length of the separation channel 2.

It should be noted that the above described scenario, including the nature of the applied electric field and that of the hydrodynamic force on the object 10, is merely exemplary and intended to illustrate the principles of the invention without limitation. In practice, the shape of the electric field profile will be selected as appropriate for the particles 10 to be separated. Depending on this shape, the dynamic range (in terms of charge and friction coefficient) of the objects that separate with a given resolution in a given channel length can be specified.

For example, if a sample contains objects which occupy the large sizes (large friction and charge) more sparsely compared to the small sizes (small friction and charge), then selecting a "concave down" field profile such as that shown in FIG. 2b will "compress" the larger sizes closer together, while the more densely populated small sizes will be placed further apart. This achieves higher resolution at the more dense region where it is required, allowing the user to "zoom in" on a particular section of the band train. Which sections are compressed and which are expanded depends on the sign of the field profile's curvature.

Common to all the embodiments however is the use of an electric field profile which, over time, is adjusted relative to the separation channel 2. This leads to the charged objects 10 being continuously subjected to electric force which imparts to them motion relative to the fluid 9. As a result, a hydrodynamic force is continuously applied by the fluid. It is a combination of these forces which leads to efficient separation and, importantly, bands which do not diffuse with time.

In the preferred embodiment, there is no flow of the fluid 9 through the channel 2. This eliminates the problems associated with a parabolic velocity front previously discussed, and allows the device to achieve much higher resolution. The need for an expensive pumping network is also removed. However alternative embodiments are envisaged in which there is some fluid flow through the channel. This could be advantageous in cases where the electric field would otherwise have to change unfeasibly fast to achieve effective separation. However in the majority of cases it is expected that the elimination of fluid flow would have greater benefits.

That said, fluid flow may be established (intentionally or unintentionally) in the channel by electro-osmotic flow ("EOF"). This is a phenomenon caused by the combination of the applied electric filed with the electric properties of the fluid and those of the internal surface of the separation channel. As in conventional electrophoresis systems, EOF is stopped or controlled to an optimum value (which may be zero) by selection of appropriate surface chemistry. Interactions between the channel walls and the fluid are chemically controlled by treating the walls of the channel. The electric field configuration may also be modified to take EOF into account.

Figure 6:
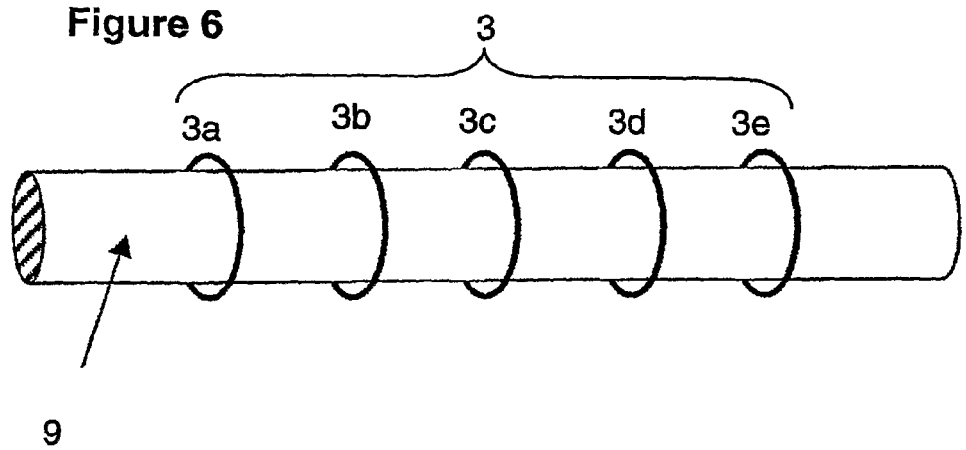
FIG. 6 depicts a first embodiment of a portion of an electrophoretic device for separating objects.
Figure 7:
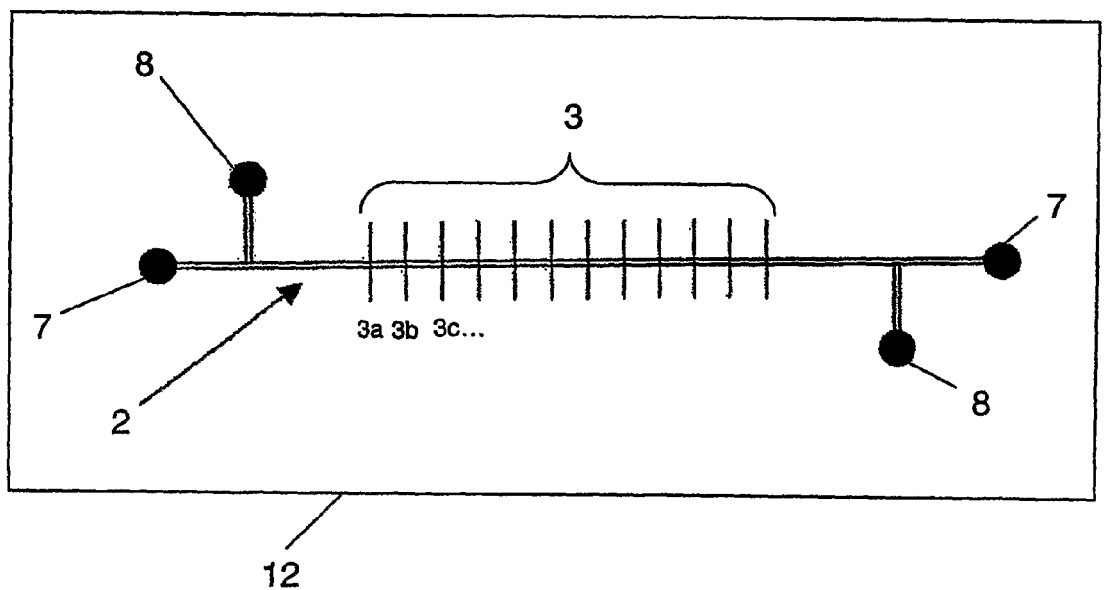
FIG. 7 depicts a second embodiment of a portion of an electrophoretic device for separating objects.
Figure 8:
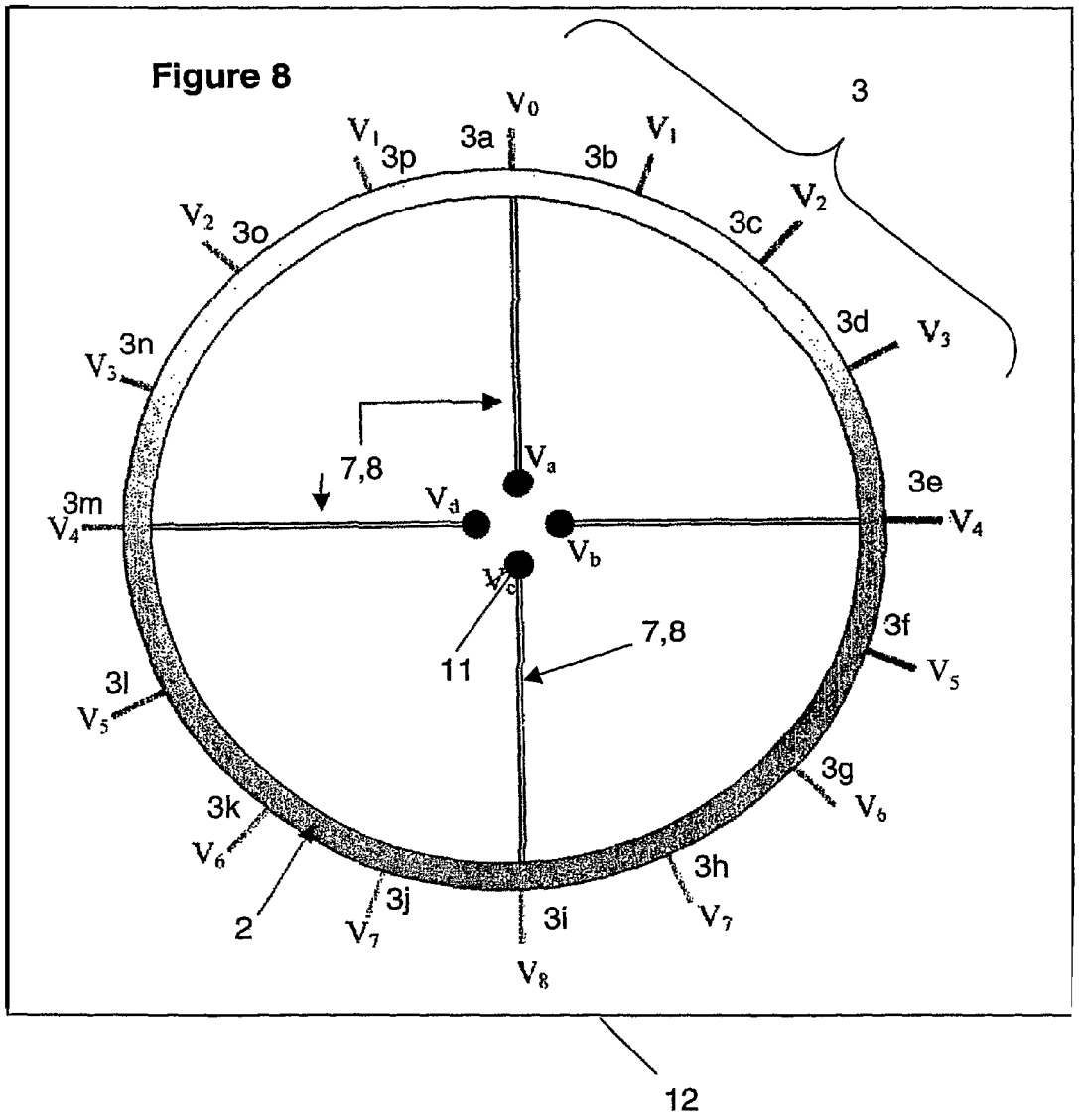
FIG. 8 depicts a third embodiment of a portion of an electrophoretic device for separating objects.

FIGS. 6, 7 and 8 show three preferred implementations. The separation channel 2 may be provided in a number of different forms, although in each case it is preferable that it be disposed substantially horizontally (i.e. the channel 2 should lie in a horizontal plane). This avoids gravitational forces interfering with fluidic processes. In the embodiment of FIG. 6, the separation channel 2 is a capillary tube which in use contains the fluid 9 and a sample including the objects 10 to be separated. A section of the separation channel 2 is encircled by a series of annular electrodes 3a to 3e, which provide the means 3 for applying an electric field along the channel 2. The voltage on each electrode 3a to 3e is controlled by controller 4 (FIG. 1). It should be noted that the number of electrodes depicted in the Figures is merely exemplary.

FIG. 7 shows a second embodiment in which a microfluidic separation channel 2 is provided in the form of an engraved channel in a substrate 12. The substrate 12 could be a glass, quartz or polydimethylsiloxane (PDMS) plate or a semi-conductor chip for example. An array of electrodes 3a, 3b, 3c etc is disposed along the separation channel 2 and forms the means 3 for applying an electric field along at least a section of the separation channel 2. Wells 7 and 8 provide input and output ports for introducing the sample to the separation channel 2 and/or extracting parts of it from the channel 2. This will be described in more detail below.

The electrodes 3a, 3b, 3c etc are controlled by a controller 4 so as to provide a time dependent electric field. Objects inside the separation channels separate to form bands inside the separation channel moving with a (preferably) constant velocity. In the above-described linear implementations, the electric field may be caused to oscillate so that the bands move back and forth along the channel 2 allowing multiple detection of the same band. This can increase sensitivity for low concentration components.

As an alternative to linear implementations, the separation channel 2 could be provided in the form of a closed loop, an example of which is shown in FIG. 8. The loop could be circular (i.e. having a circular plan view as shown in FIG. 8), but it may in fact be beneficial if the channel 2 has straight sections, especially in the detection region. Electrodes 3a, 3b, 3c . . . 3p are provided at intervals around the channel 2 to make up the field generating means 3. Generally, the electrodes are placed in a symmetric manner as shown in FIG. 8. The applied voltage may also be symmetric, as indicated by values $V_0$ to $V_8$ as shown in FIG. 8.

When a time-varying electric field is applied, the objects 10 (assuming they have charge of the same sign) either on the left or right semicircle separate, moving either clockwise or anti-clockwise. The molecules in the opposite semicircle do not separate but move in an erratic manner until they enter into the other semicircle. This is because the molecules in one semicircle will experience an electric field gradient which is incorrectly aligned with the time-dependence vector k. A given set of electric field parameters will only allow a range of charge and friction values to separate in a given separation length. When the migrating molecules that fall within this range have completed a full circle, all these molecules move in sync and are separated into bands. The resulting train of bands rotates continuously around the channel 2 and can be detected repeatedly.

Figure 9:
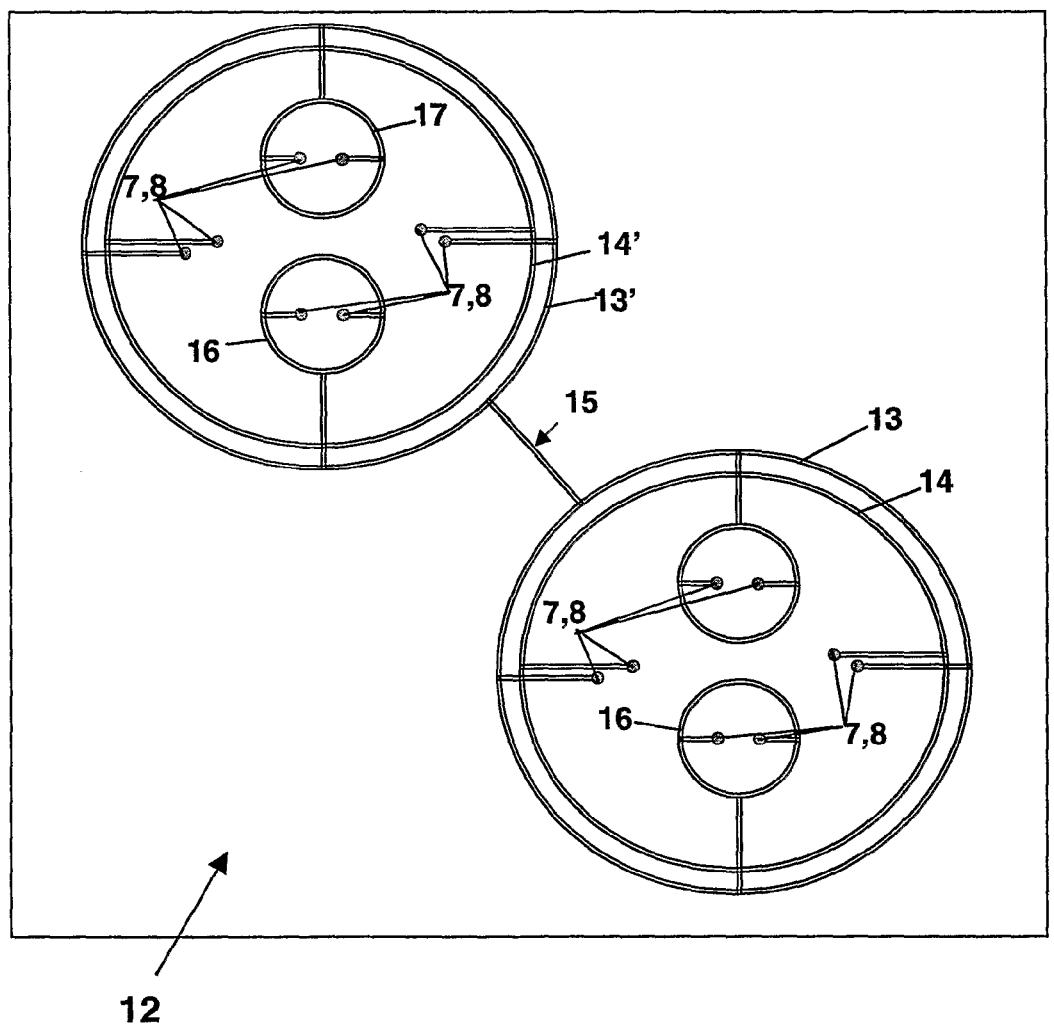
FIG. 9 shows a the configuration of a separation channel for a fourth embodiment of an electrophoretic device for separating objects.

The separation channel 2 can be straight or bent or a combination of both. The same principles apply to either configuration apart from a velocity correction that is needed for curved channels (see below). FIG. 9 shows an example network of an embodiment having both straight and curved channels. In this example the separation takes place in the circular channels 13, 14. One separation strategy could be that there are many concentric circles (or many parallel linear channels) which are fluidically connected at various points. The field parameters on the outer circle 13 (or first linear channel) are set to given initial conditions to achieve and initial separation in this channel that perhaps shows the big picture (wide friction-charge space). Then individual windows of this space are cut out as they pass next to transport channels 15 (see FIG. 9) and they are transported to a neighbouring separation channel 13' with different settings for the electric field so as to focus the separation to this selected window of friction-charge. In this manner many windows can be selected and transported to different separation channels with field settings that optimise the separation of this specific part of the sample. DNA sequencing for example can be automatically split into base-pair ranges and sequenced separately up to a very high base pair read.

Other strategies can be involved with different macromolecules. For example some rings 16 can be labelled as storage rings where separated proteins are transported and stored in a desirable buffer environment. Other rings 17 could be used as mixing channels. There can also be "reaction rings" (or channels) where the transported macromolecules are exposed to desired chemicals where they react as they move along the separation channel. The product of the chemical reaction can be automatically separated from the parent molecule through the standard separation principle and visualised in real time as the reaction is going on.

In addition the temperature and other environmental parameters can be controlled in each ring (channel) in order to have controlled reactions. For example, protein folding can be monitored by increasing the temperature gradually in a channel where proteins are separated. At a given temperature, the proteins will unfold and this event will be observed through the alteration of the electrokinetic characteristics of those proteins as they move along the separation channel.

Sample collection and injection wells may be placed at selected positions along the separation channels or rings for the following purposes (amongst others): Channel filling with gel or buffer, channel flushing with chemicals, sample injection, sample collection and others.

Figure 11:
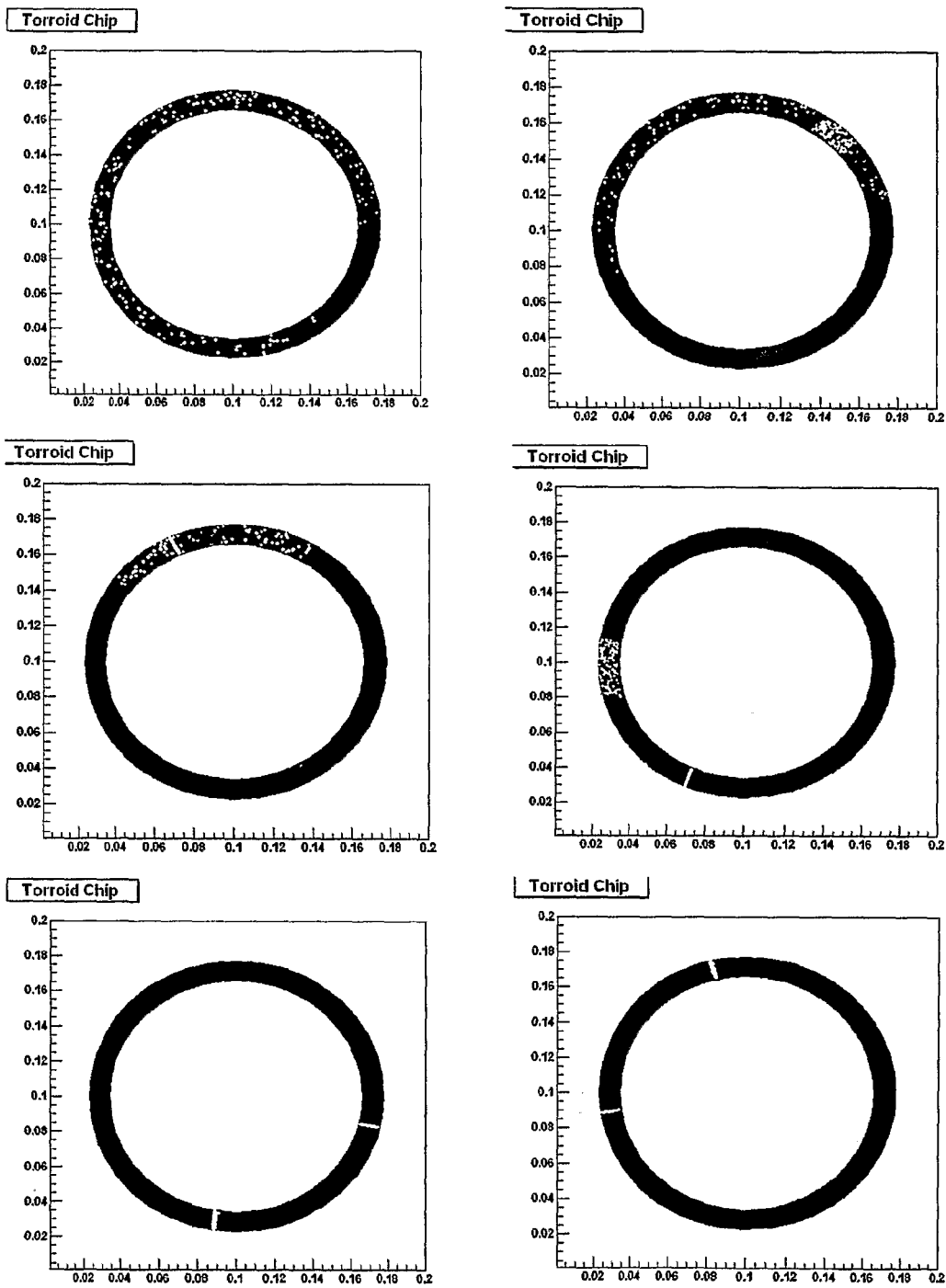
FIG. 11 illustrates band separation in a curved channel with velocity correction.

In curved separation channels (for example circular), molecules that move at the outer perimeter of the channel must move faster than molecules that move at the inner perimeter in order to stay in phase and coherent bands to be formed. If no such velocity correction is applied, the molecules that move close to the outer perimeter become out of phase with those at the inner perimeter and the bands form an expanding spiral pattern (FIG. 10). This can be prevented by deploying electrodes at either side of the circular channel. The electric field applying means 3 is controlled such that the outer electrodes will implement the time varying field with a slightly higher parameter $k_{outer}$ compared to $k_{inner}$ that is produced by the inner electrodes. In most cases, it is sufficient if inner and outer electrodes at the same angular position are in phase, i.e. they carry the same voltage at any one instance. Where different voltages are applied to the inner and outer electrodes, due to the small distance between the outer and inner electrodes, the slightly different fields will interpolate between the two electrodes creating intermediate field values for the locations between the outer and inner perimeter, resulting in coherent bands as shown in FIG. 11.

It should be noted that if the electrodes extend radially (i.e. each electrode is arranged so as to intersect the inner and outer perimeter of the separation channel, and points toward the centre of curvature), an automatic correction of k may also be achieved. This is because the train of voltages on the electrodes will complete a full cycle in a given time period, regardless of the radial position.

It will be appreciated that a non-linear voltage distribution is required to establish an electric field profile (as described above) within the separation channel. In order to implement this in each of the above embodiments, it is proposed that the time varying electric field profile be applied along the separation channel by an array of electrodes $3a$, $3b$, $3c$ etc. The electrodes may be in non-electrical contact with the separation buffer but very close to it. Such an array of electrodes would generate a static electric field inside the separation channel. The advantage of this configuration is that firstly the power consumption by the power supply is very low as no electric current flows between the electrodes. Secondly the electrodes can be placed at a (small) distance from the separation channel in order to smooth the local effects on the field caused by the discrete nature of an array of electrodes. In fact the further away the electrodes are from the separation channel, the smoother is the electric field inside the channel.

However there is a disadvantage with this configuration. The application of a static field on a polar dielectric like an aqueous buffer, is damped by the dielectric coefficient which for aqueous solutions is usually around 80. For effective generation of the field inside the fluid, one has to take into account the rate of change of the field, the dielectric constant, and the conductivity of the medium. Typically, the electric field that is generated inside water is 80 times smaller than the field that would have been generated in air (dielectric coefficient 1) by the same electric charge. This means that in some configurations of the device, very high voltage would need to be applied. This would require special HV supplies and careful consideration of the dielectric material where the electrodes would be implanted, to avoid dielectric break down and the formation of sparks between the electrodes. This problem can be avoided by the use of electrodes which are in electric contact with the separation buffer. It is much easier to generate high electric fields by generating an electric current in a conducting separation buffer.

Figure 12:
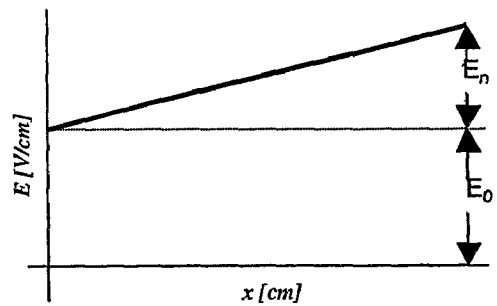
FIG. 12 is a graph illustrating a dual electric field gradient.
Figure 13:
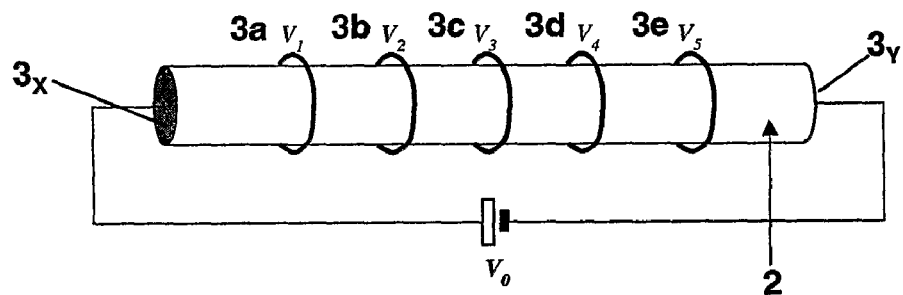
FIG. 13 shows a first exemplary electrode configuration.
Figure 14:
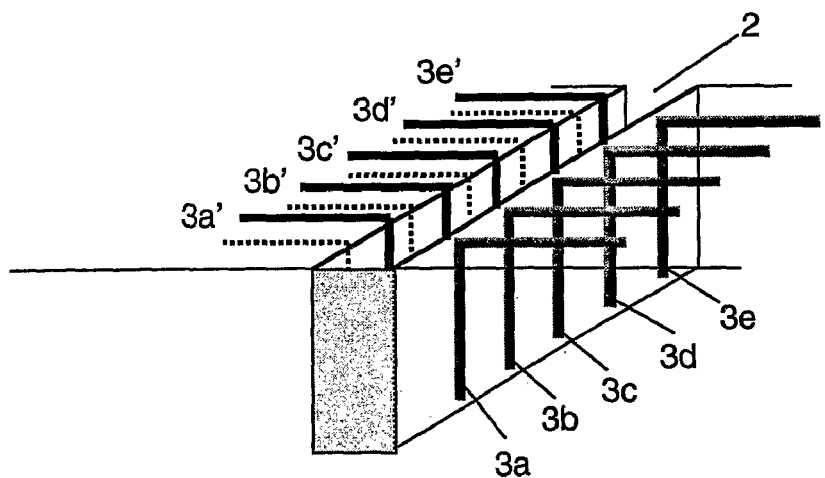
FIG. 14 shows a second exemplary electrode configuration.

In order to improve field generation, a combination of external (non-contact) and internal electrodes may be deployed. For example, as is shown in FIG. 12, in most cases the field gradient along a channel at any time instant consists of a constant and a varying part. The constant field $E_0$ (which in most cases will be the largest by far) can be achieved through the application of a voltage between two electrodes, $3_x$ and $3y$, at the opposite ends of the separation channel. Then the gradient $E_n$ can be added by an array of external electrodes along the separation channel as shown in FIGS. 13 and 14. In FIG. 14, electrodes 3a, 3b, 3c etc are external, ie. close to but not in contact with the fluid, and electrodes 3'a, 3'b, 3'c etc are internal, ie. in electrical contact with the fluid.

Figure 15:
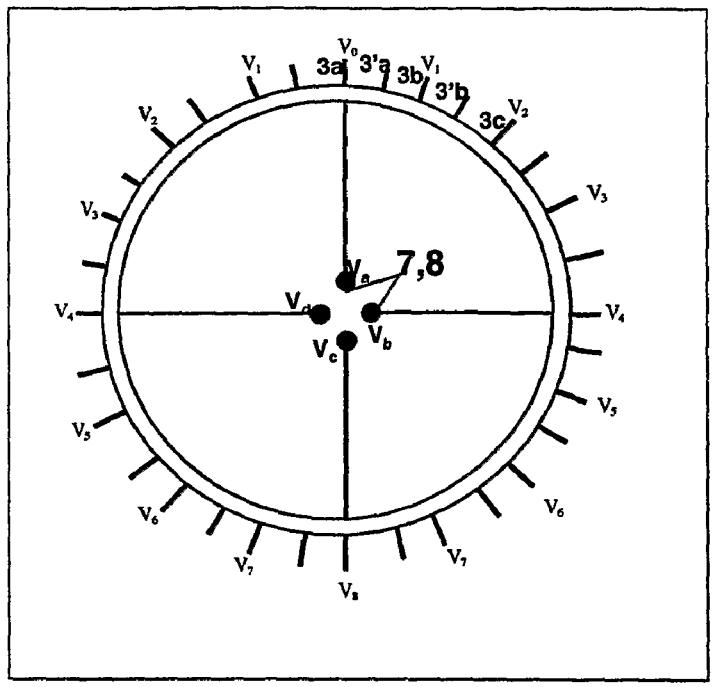
FIG. 15 shows a third exemplary electrode configuration.

In the case of a circular channel, it is not clear which are the "ends" of the separation. In fact the two opposing internal electrodes have to rotate around the channel in phase with the separation. Therefore an array of internal electrodes is needed in this case. Note that in principle and at every time instance only two of the internal electrodes will carry voltage. Those two electrodes can be at diametrically opposite positions. FIG. 15 shows such a configuration of alternating internal and external electrodes. The external electrodes generate a static field gradient which is time-dependant and creates the special separating principle of the device. The static field is added to the constant field created by the internal electrodes.

FIG. 14 shows an arrangement of alternating internal and external electrodes along a microfluidic channel. Note that both internal and external electrodes can be arranged along either side of a separation channel, or may hermetically surround it to achieve the smoothest possible electric field along the channel.

It is possible to create the electric field solely by an array of internal electrodes. However, the electrodes that are in electric contact with the separation buffer are expected to create significant distortions to the electric field at the locus of each electrode along the channel. The separating molecules would pass at very close proximity (contact) to the electrodes, "feeling" the field distortions. This would degrade the resolution. In the case of generating only a constant field by using only two electrodes at either end of the channel (conventional electrophoresis), the same problem does not exist because the molecules separate between the electrodes and are never in close proximity to them.

In fact, since the electric field variations along the channel are quite subtle, in some cases the distortions caused by an internal electrode array can have a significant impact on the separation principle of the system herein disclosed. In addition, the longitudinal size of the electrodes can play an important role. For example, if we assume flat electrodes of approximately 100 μm in length (along the channel), the electric field between two opposing electrodes with the same voltage will be zero. This is because the voltage is not varying longitudinally (along the channel) in the space between opposing electrodes, and therefore the electric field tends to drop to zero in that area. This exacerbates the local distortion caused by the internal electrodes.

However, as discussed above, the use of internal electrodes has a significant advantage in the sense that it requires much simpler electronics and lower voltages.

Figure 16:
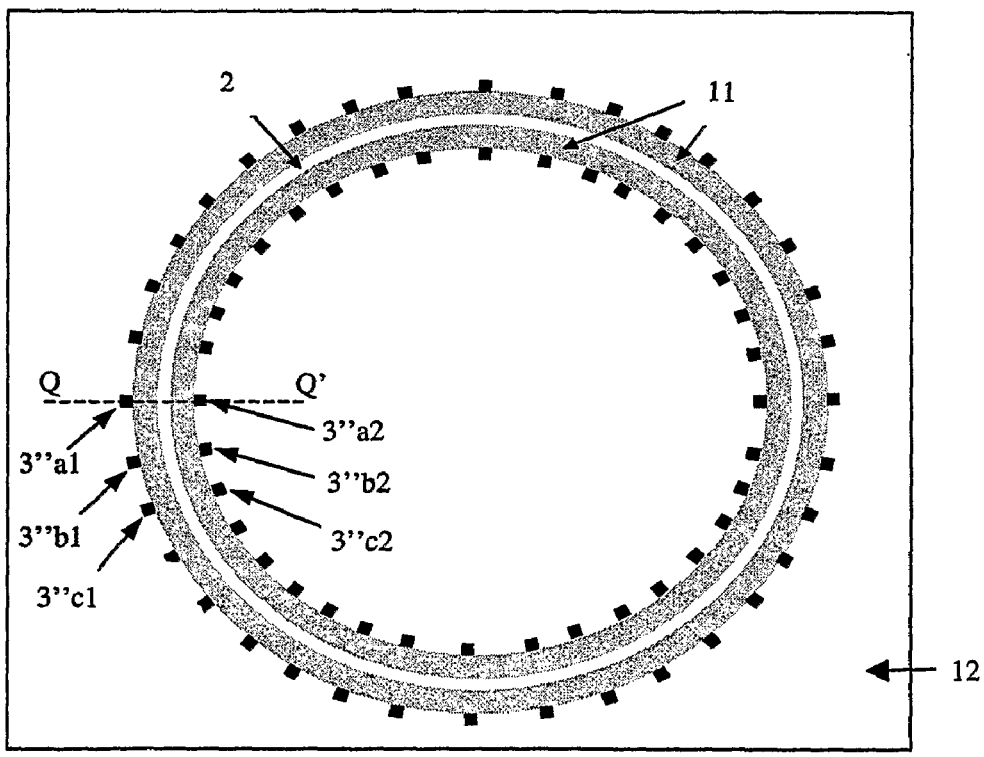
FIG. 16 shows a fourth exemplary electrode configuration.

One way to reduce the local distortions caused by the internal electrodes is to deploy a resistive medium between the electrodes and the gel in the separation channel. Therefore, in a further example, multiple electrode points could be disposed along the channel, connected with a material which has a electrical resistance. An array of voltages is applied at each point, and the resistance between the points interpolates the fields between two points creating a smoother field. FIG. 16 shows an example of such a configuration in which two semiconductor layers 11 are used to substitute the side walls of the channel 2. The electrodes 3"a1, 3"a2, 3"b1, 3"b2 etc are positioned on the outside of these resistive layers 11, which have the effect of smoothing out the electric field generated inside the separation channel 2. The resistive material 11 could be doped silicon or any other medium that would have the desired properties in terms of resistivity and dielectric constant. Doped semiconductors are attractive because the resistivity can be controlled over many orders of magnitude. Furthermore, such materials usually tend to be biocompatible (i.e. chemically inert), and for silicon especially, the available technologies for creating microstructures are inexpensive and widely available.

FIG. 17 shows a cross-section of the configuration illustrated in FIG. 16 along the line Q-Q'. The separation channel 2, containing separation medium 9, is shown at the center of the cross-section, with a layer of resistive material 11 disposed on either side. The inner and outer electrodes 3"a1 and 3"a2 are located at the outer sides of resistive layers 11, such that the resistive material lies between the electrodes 3"a1, 3"a2 and the separation channel 2.

We have used a finite element algorithm to calculate the field shape and its smoothness with and without the resistive layers 11. In a first example, platinum electrodes were placed at the side walls of the separation channel 2, without resistive layers 11. The distance between the electrodes was 1 mm and their longitudinal (z-direction) size was 100 μm. FIG. 18A shows this arrangement in plan view, illustrating the gel-filled separation channel 2 and three pairs of electrodes 3"a2 etc in electrical contact with the gel 9. FIG. 18B shows the electric field vectors inside a section of the separation channel 2 as calculated by the finite element algorithm. It is evident that in the neighbourhood of the electrodes there is significant deviation of the field from the longitudinal direction.

Figure 18C:
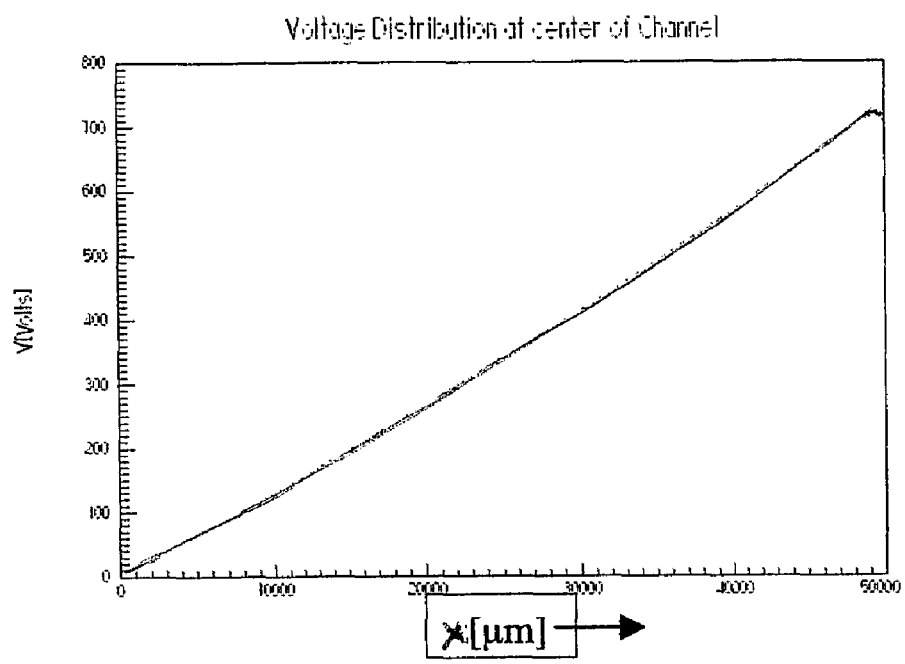
FIG. 18C is a graph showing the voltage distribution along the centre of the channel depicted in FIG. 18A.

FIG. 18C shows the voltage distribution along the centre of the channel 2 (along the line that is placed at the centre of the cross-section of the channel 2 and runs parallel to the x-direction). The voltage range is consistent with the range of values attached to the electrodes (0 to 700V). The shape of the line follows the equation $$V=1/2kx^2+cx \qquad (2.1)$$

which gives a linear field $$E=-kx-c \qquad (2.2)$$

Figure 18D:
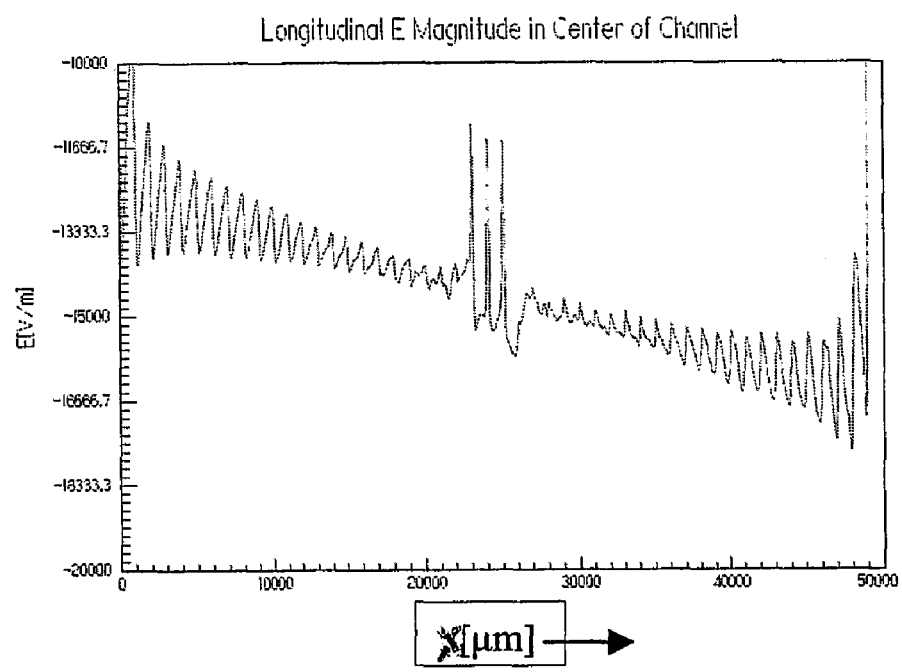
FIG. 18D is a graph showing the electric field distribution along the centre of the channel depicted in FIG. 18A.

However, FIG. 18D, which depicts the corresponding longitudinal electric field distribution along the channel, shows that the electric field distortions in the vicinity of the electrodes are very evident.

Figure 19A:
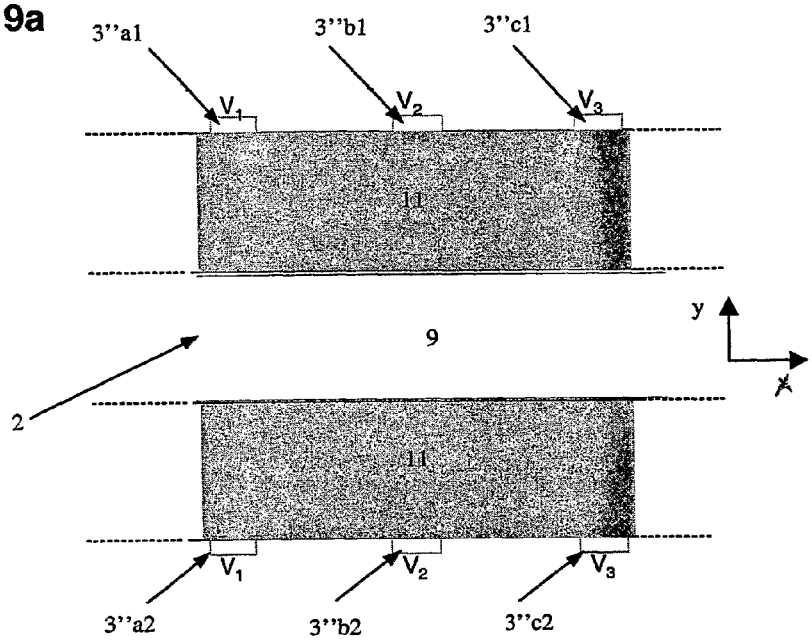
FIG. 19A schematically depicts a portion of a sixth exemplary electrode configuration in plan view.
Figure 19B:
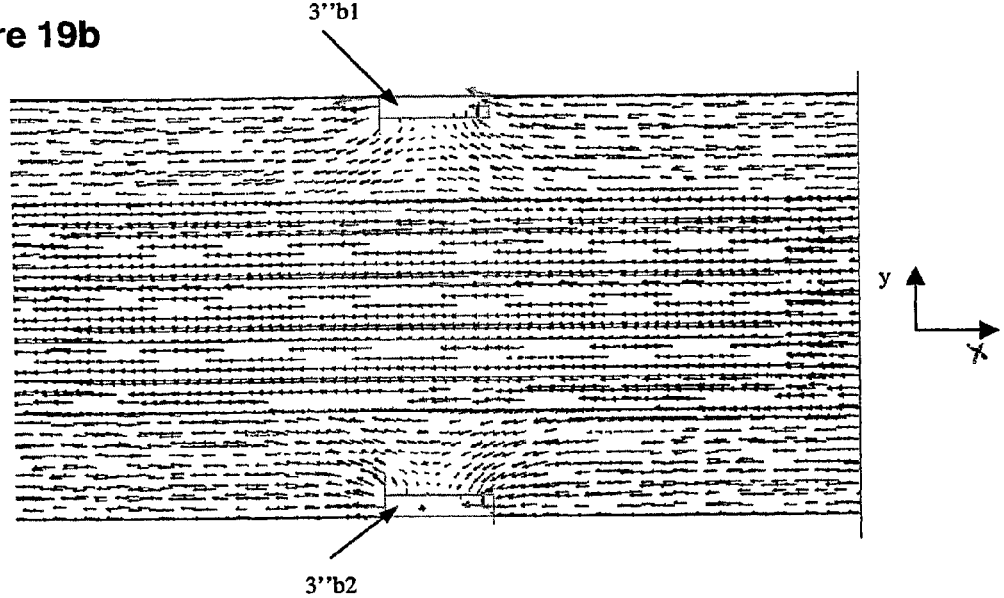
FIG. 19B shows the electric field lines calculated for the sixth electrode configuration.
Figure 19C:
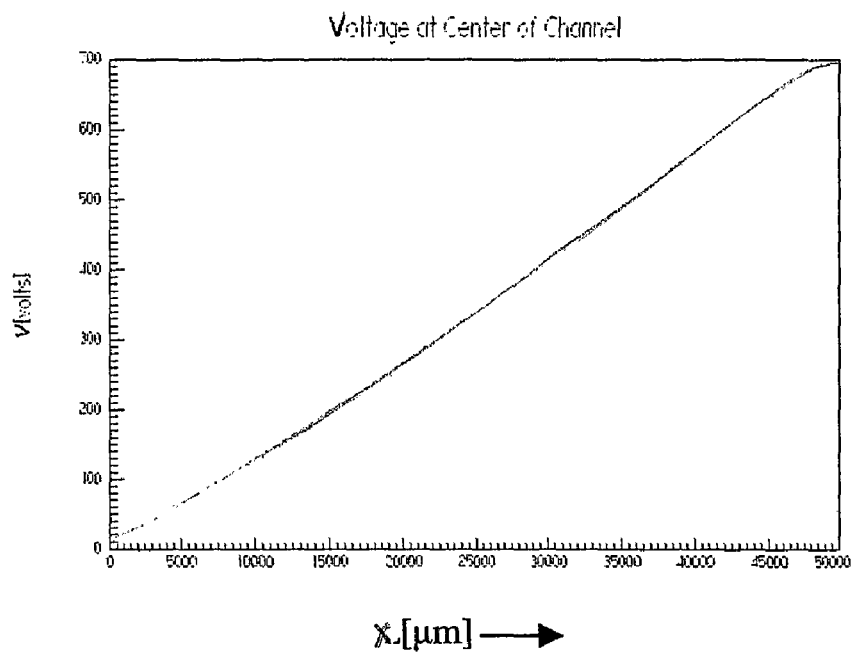
FIG. 19C is a graph showing the voltage distribution along the centre of the channel depicted in FIG. 19A.
Figure 19D:
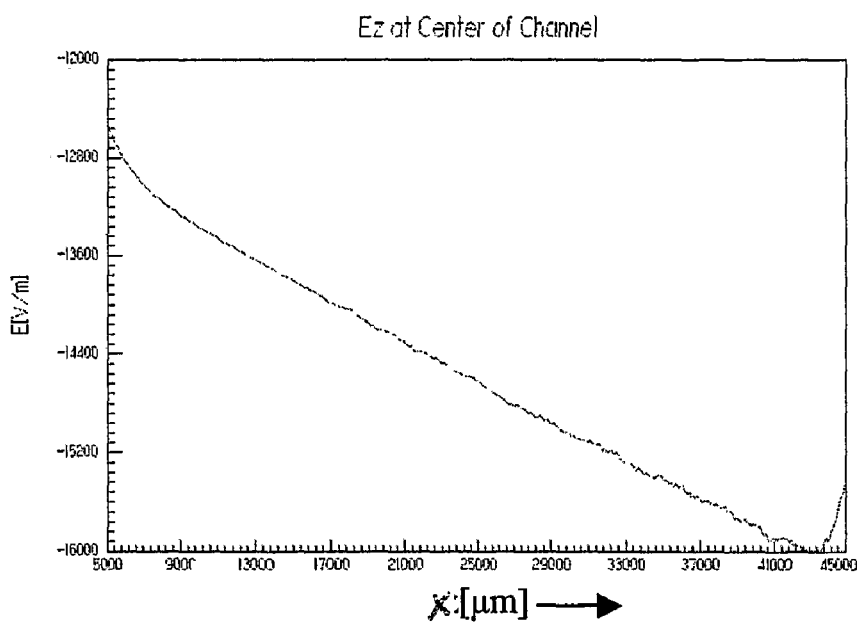
FIG. 19D is a graph showing the voltage distribution along the centre of the channel depicted in FIG. 19A.

In a second example, shown in plan view in FIG. 19A, 1 mm thick resistive layers 11 are placed at the sides of the separation channel 2, which essentially form the walls of the channel 2. The resistivity of the material in this example is 80 Ωm. The electrodes 3"a1, 3"a2 are 20 μm wide (along the z-direction), and they are placed at 1 mm intervals along the outer wall of the resistive material 11. FIG. 19B shows the electric field vectors calculated for this configuration. It can be seen that the field distortions are confined within the resistive layers 11, and the electric field vectors inside the separation channel 2 are pointing dominantly along the z-direction. FIG. 19C shows the voltage distribution along a line at the centre of the channel 2 running parallel to the x-direction. Again, the range of voltage is consistent with the voltage of the electrodes, and the voltage distribution follows a second-order power law. FIG. 19D shows the electric field shape, which is now free of the intense oscillations generated with the setup shown in FIG. 18.

Internal electrodes may also be placed at strategic positions near transport channels to switch protein or DNA bands out of the separation channel and transport them to neighbouring channels of separation rings. For instance, in the configuration shown in FIG. 15, the same array of internal electrodes can be used for the dual purpose of applying the constant field and for switching bands from the separation ring to the transport channel on the way to another ring or collection well.

The electric field applying means 3 may consist of conductive wires fixed along the separation channel 2 (or the resistive layers 11). Alternatively the electrodes may be produced using etching methods similar to electronic PCB boards or by using conductive ink. The latter method is especially attractive as very thin electrodes may be printed in complex configurations. The electric field could also be applied by means of a varying resistance along the channel. It would also be possible to provide a movable array of electrodes, or other field generating means, which could be controlled so as to move relative to the separation channel 2.

In each of the above described embodiments, the electrophoresis device may be provided with a detector 6 for detecting the bands of separated objects once they have formed. Typically, the detector 6 generates an image of the separated bands. There can be a variety of imaging systems which are more suitable for different requirements, e.g. cost, accuracy, and different samples. The possibility to run label free (unstained) samples is generally the more attractive option as it leaves the samples unmodified to a certain extent. Further the use of stains is undesirable since substances which attach to DNA or proteins will generally also adhere to a user. In addition the costs are lower since one preparation stage is removed. Also the preparation time is reduced for the same reason.

Figure 20:
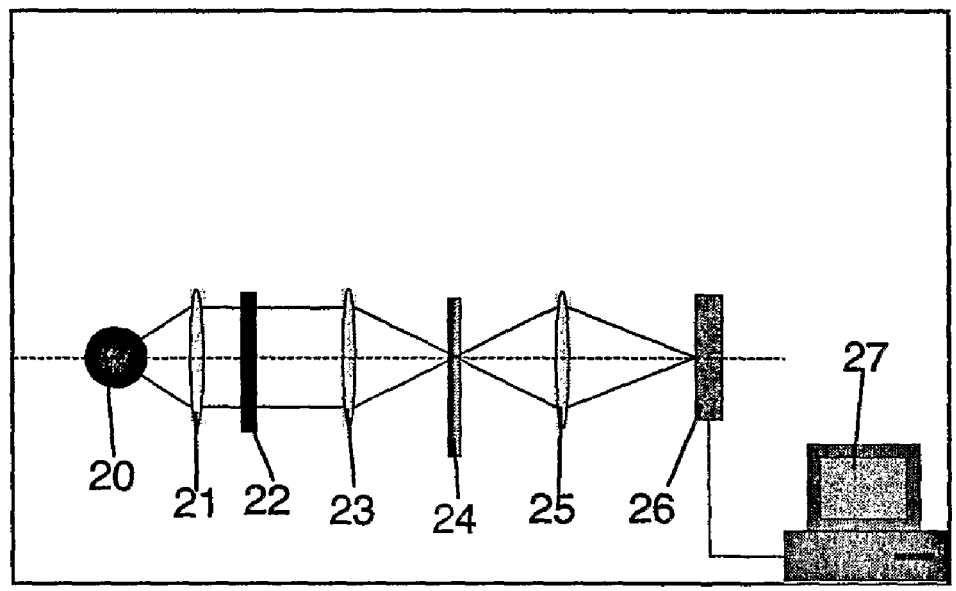
FIG. 20 shows a first embodiment of a detector for use with an electrophoretic device for separating objects.
Figure 21:
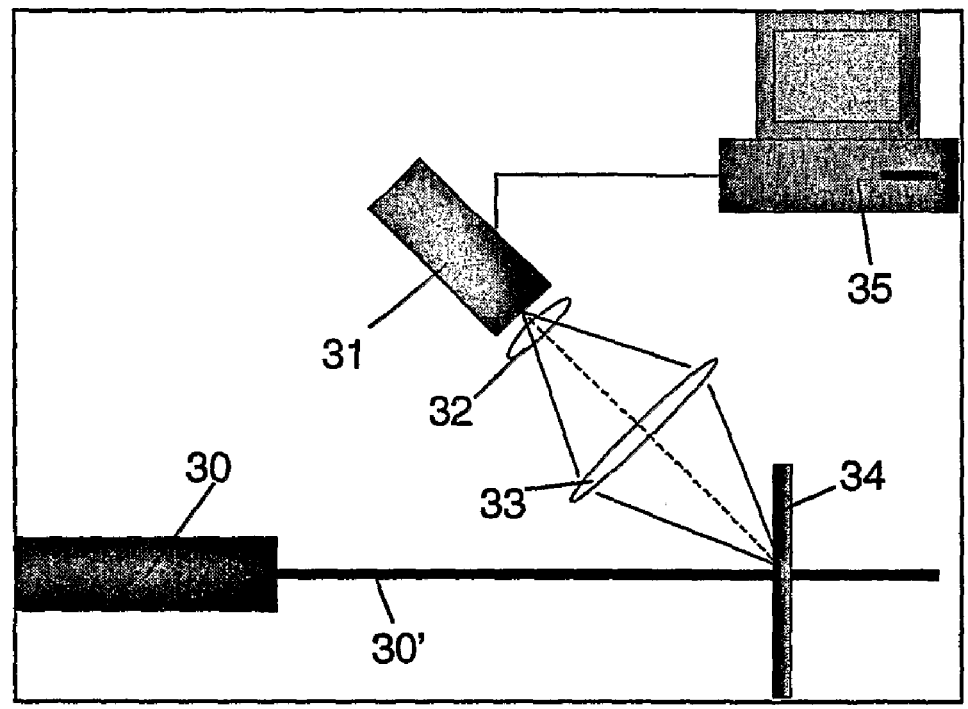
FIG. 21 shows a second embodiment of a detector for use with an electrophoretic device for separating objects.

Two methods for label-free detection will now be described. FIGS. 20 and 21 show example implementations of UV absorption and Laser Induced Fluorescence (LIF) techniques respectively. It should be noted that other configurations involving fluorescence detection for stained samples can also be deployed for imaging. In general, the light patterns, whether from absorption or fluorescence can be detected by a photodiode, pixel detector (CCD for example) or photomultiplier (PMT).

FIG. 20 shows a UV absorbance configuration. A UV light source 20 emits light which passes though condensing lens 21, focussing lens 23 and imaging lens 25. The light is filtered by the interference filter 22 and focussed on the microfluidic channel 24. The absorption image is detected by a photodiode or pixel detector 26 and digitised by a PC 27.

FIG. 21 shows a laser induced fluorescence (LIF) configuration. A laser 30 shines UV wavelengths 30' on the microfluidic channel 34 and causes the macromolecules in the separating bands to fluoresce at a wavelength. The interference filter 32 is tuned to this wavelength window. The photodiode 31 is placed at an angle in relation to the laser line. The optics 33 allow for the photodiode to detect a conical section of the fluorescence light. The emission signal is digitised by a PC 35.

In each case, the signal is transferred to a computer 27 or 35 containing an Analogue to Digital Converter (ADC) which is responsible for the digitisation of the signal. Control and analysis software analyses the images in real time.

In conventional electrophoresis, as mentioned above, the relative distance between the bands increases with time, because they move with different terminal velocities. Therefore it is logical to image only the last section of the separation, where the bands have reached their maximum relative distance. In contrast, the proposed method achieves separation very early on, therefore the imaging can take place at any point along the separation channel or even, many points along the channel may be imaged using a pixel detector arranged longitudinally along the separation channel. The detector can be interrogated by the readout electronics (which may be incorporated in the controller 4) many times per second, thus giving an array of frames describing accurately the motion of the bands along the channel. Having a multitude of pixels along the separation channel is not necessary in most embodiments, however in some occasions it may be advantageous to have a dynamic picture of the ongoing separation. In other embodiments, a CCD may be used to image a larger area of a multichannel microfluidic or capillary system. The detector and imaging optics can be arranged in such a way so as to image simultaneously a multitude of separation channels where simultaneous runs are taking place. This makes it easier to perform comparative analyses between the different channels, in real time or after the separation runs are completed. An additional advantage of using such an optical and detector arrangement is that only one readout circuit may be involved helping reduce the systematic noise induced on the imaging, by multiple circuits.

The input ports 7 are typically provided in the form of wells, arranged for receipt of an injected sample. The output ports 8 typically comprise wells equipped with electrodes which can be activated by the controller 4 in order to draw the desired components out of the separation channel and into the output port when the selected portion of the sample passes in front of the exit point.

It is further envisaged that the device could be provided with more than one separation channel 2. In this case, each channel would be provided with means 3 for applying an electric field along that channel and a controller for controlling the field. Conveniently, one controller could control several (or all) of the channels and it may also be possible to share the field applying means between channels. Each channel could be provided with a detector and input and output ports as previously described.

Each channel could be controlled so as to experience the same electric field variation. However, if the contents of each channel are different, it may be beneficial to control the field applied to each channel individually.

The operation of the electrophoretic device, according to any of the above embodiments, will now be described. In the following description, the term "sample" is used to describe a mixture of the objects 10 to be separated with a volume of the separation fluid 9. Typically, the sample is prepared by mixing the objects to be separated with the fluid and it is then used to fill the separation channel 2. Typical objects to be separated include macromolecules, biomolecules or polymers such as proteins, DNA molecules or biological cells. The separation fluid may be a buffer (example composition: Tricine, bovine serum albumin and n-octyl glucoside) or a gel such as polyacrilamide.

Figure 22:
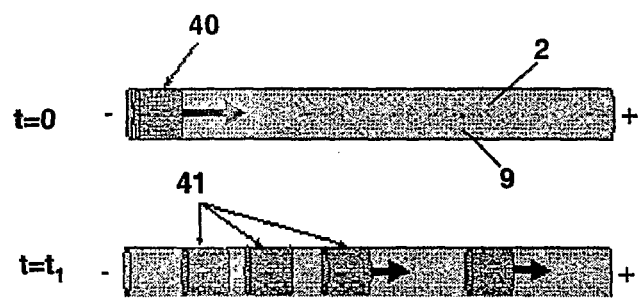
FIG. 22 schematically depicts the step of introducing a sample to a separation channel using conventional techniques.

A further advantage of this device over standard electrophoretic or chromatographic techniques is the fact that no sample injection plug is required. In conventional capillary electrophoresis for example, when sample injection takes place, then firstly the one end of the capillary is submerged into a container that contains a DNA or protein solution. Then electrodes are also submerged into the sample container and waste container to form a closed circuit through the capillary. The electric field that forms pulls an amount of DNA or protein into the capillary. The application of the voltage is stopped, and the sample container is replaced by a container that only holds a salt solution. The voltage is reapplied and the little sample plug 40 (FIG. 22) that had formed at the entrance of the capillary starts moving and separating. This is the standard method for sample injection. Note that the separated bands 41 are directly influenced by the initial width of the sample plug. This width is further increased by thermal diffusion.

Figure 23:
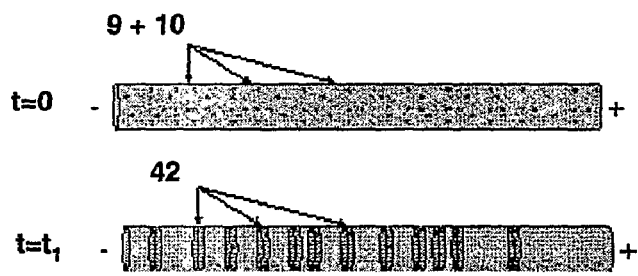
FIGS. 23 and 24 show two methods of introducing a sample to a separation channel which may be employed in the use of an electrophoretic device as herein disclosed.
Figure 24:
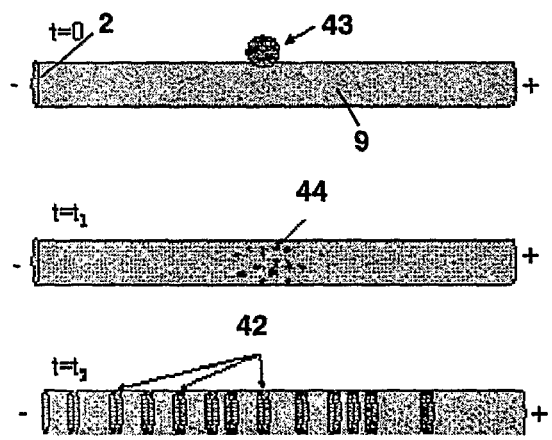

The present device however does not need a sample plug as such. The DNA or protein sample can be mixed with the sieving gel or buffer prior to its introduction into the capillary (FIG. 23). Alternatively, the separation channel 2 could be prefilled with fluid 9, and the objects 10 or sample to be separated introduced at a later stage prior to the commencement of the separation process. A drop 43 of sample can be introduced randomly anywhere along the separation channel (FIG. 24). The sample drop 43 diffuses into the fluid 9 over an area 44. The time-varying field will "collect" all sample molecules and sort them into bands 42 along the channel with high resolution. Such a "random-incoherent" injection is ineffective in standard Chromatographic or Electrophoretic processes. The reason is that there is no mechanism to make a coherent band if one starts from an incoherent. In fact the size of the injection plug is a crucial concern as it directly affects the resolution.

For example current commercial devices deploy electrokinetic injection (as described above, FIG. 22) or pressure injection (instead of using voltage to pull in the plug, pressure is used). The reason why two different methods are used is precisely because each method gives slightly better resolution in different configurations.

The device herein disclosed is not dependent on any such injection plug. This is why it allows for alternative injection methods compared to standard technology. The sample may be loaded to the separation channel either by mixing it in advance with the separation buffer (or sieving gel), or by pressure injecting it through an entry well. Alternatively the sample can be placed inside a well or container and injected into the separation channel by using standard electrokinetic injection. This means that one electrode is submerged into the well that contains the sample and there exist an electrode at the other end of the transport channel. By applying an appropriate voltage between the electrodes the sample is electrically attracted out of the well, through the transport channel and into the separation channel.

An alternative injection method would take advantage of the special nature of the device, that does not require a coherent injection plug. A drop of sample is simply placed by a syringe-like instrument at any point along the separation channel simply on the surface of the buffer or sieving gel (see FIG. 24). Subsequently the drop will diffuse incoherently into the buffer region 44 close to the injection point. Once the drop was placed on the buffer as it diffuses through it the varying electric field will immediately affect the molecules and the separation process will have been initiated.

The syringe-type instrument can be transferred to an exposed part of the separation channel, either by hand, or automatically by a robotic arm that is controlled by special software.

An electric field having a field profile of appropriate shape and intensity is applied via the field generation means 3 along the separation channel 2. The electric field is varied by the controller 4 so as to produce a time dependency which adjusts the field relative to the separation channel and so causes the molecules to separate into bands as previously described. The bands can then be imaged, or otherwise detected, by the detector 6 and the device generates a corresponding output 5. Detecting or imaging could take place after band formation or during separation. The signal evolution with time gives extra information, one example of which is "reaction time". For example if a polymer sample is added to a buffer environment where a chemical reaction takes place and additional bands are formed, then the "rise time" of the additional band (reaction product) can give information about the characteristics of this reaction. Also "Protein folding" is a time dependent event, and could therefore usefully be monitored as it takes place.

Once the objects 10 are separated into bands, the bands can themselves be manipulated by further adjustment of the electric field. By adjusting the time dependency and intensity of the field, as well as the shape of the field profile, the resolution and spacing of the bands may be adjusted as desired. The bands can also be repositioned, for example to allow a particular band of interest to be extracted at one of the exit ports.

In some applications, it is useful to control the applied electric field in such a way that the bands (or separating objects) move repeatedly past the detector. A further drawback of conventional electrophoresis or chromatography methods is that bands can only be imaged the single time they pass in front of a given detector. In this technique however, the same band can be imaged a multitude of times effectively increasing the "optical path" for absorption imaging. Absorption imaging is very convenient because the molecules in the bands need not be stained with a fluorescent label. The method is also inexpensive as a common UV light source such as a $D_2$ lamp or a mercury lamp are very cost effective. However absorption imaging suffers critically from sensitivity. This is because, in order to reduce joule heating, the separation channel must have a small cross section which achieves better heat dissipation. However a small cross section implies a short optical path and thus small absorption by each band. In the present device, the optical path limitation can be removed by repetitive imaging of each band. Instead, every cycle adds an amount to the optical path. This could be achieved by oscillating the applied field so that the objects move back and forth, or by cycling the objects several times around a closed-loop separation channel, for example.

In a further embodiment, the device could be adapted for continuous or semi-continuous receipt of a sample through the input port 7. The applied electric field is controlled so as to separate the objects into bands and move one or more bands of interest to or past one or more exit ports 8. The exit ports can be activated each time a band arrives such that components of interest can be extracted from the separation channel nearly continuously. In this way, the device can function as a purification system.

As has been described, we provide a electrophoresis device and method which is predicted to achieve fast, efficient separation of objects and high resolution. The technology can advantageously be combined or interfaced with microfluidic technology to achieve miniaturisation ultra-resolving, ultrafast separation devices. It should be inexpensive to produce as no costly additional parts are required. The disclosed device does not require fluid flow and therefore no expensive pumping network is needed. The resolution is much improved since it can be controlled by changing the electric field and hence can be increased arbitrarily (within an overheating limit). Time-dependent particle diffusion is eliminated, which limits the resolution of conventional devices. This improvement in resolution also allows the device to perform well at lower applied currents than those required in known systems, thus reducing Joule heating effects.

One example application of the device will now be described. Specifically a method is described to perform DNA sequencing. The first steps of extracting the DNA from an organism, the possible PCR amplification and the digestion as prescribed by the Sanger method or similar, will not be described here. The sequencing procedure is started from the point where the four reactions (A, T, G & C) are available.

Figure 25:
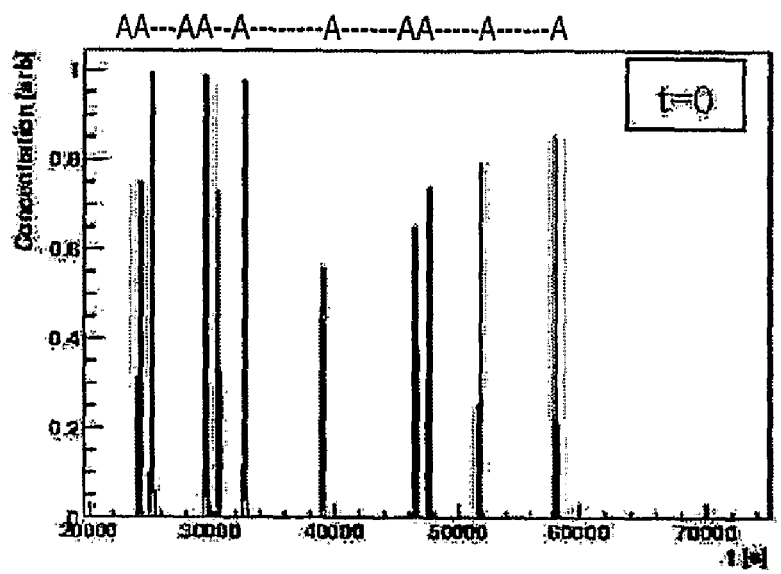
FIGS. 25 to 28 are graphs illustrating the sequencing of an exemplary DNA chain.
Figure 26:
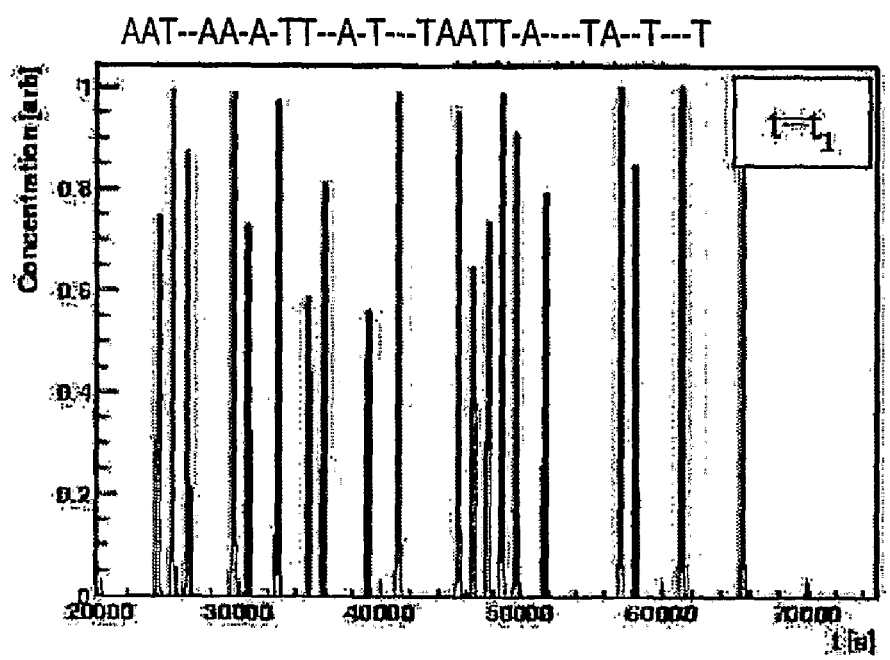
Figure 27:
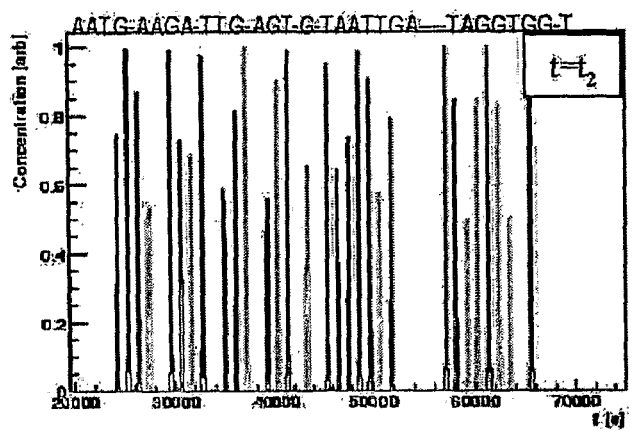
Figure 28:
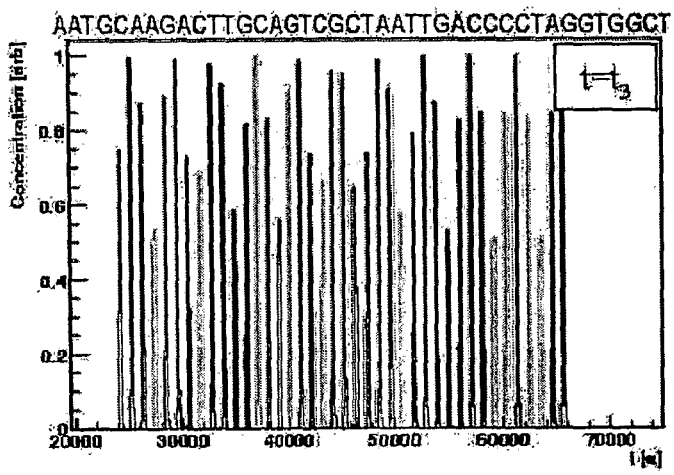

Firstly the A-reaction is placed into the separation channel containing sieving gel (for example polyacrylamide), according to the loading methods previously described. Then the time-dependant electric field is initiated and the separation of the DNA molecules takes place. The molecular bands are imaged and the result will look like a series of peaks as shown in FIG. 25. Subsequently the T-reaction is injected and the T peaks appear as shown in FIG. 24. Subsequently (and while the A and T reactions have been separated and are moving along the channel) the G and C reactions are injected in series (FIGS. 27 and 28).

In normal sequencing procedures, the four reactions need to be chemically stained with different colours in order for all four reactions to be simultaneously separated in the same channel. However the device herein disclosed overcomes this by injecting each reaction with a time delay from the previous, in the same separation channel and without using chemical stains (label-free).

By performing these sequential injections, the imaging "peaks" corresponding the DNA bands form in a time series. Firstly the "A" reaction peaks appear and automatically recorded by the imaging software. Then the "T" peaks gradually appear. Similarly the G & C peaks appear with further time delays. The timing of the peaks is a good indicator of which peak belongs to which reaction and therefore the sequencing can take place in a single microfluidic channel and without the use of staining for the DNA molecules.

Further information may be obtained by observing the formation of the bands. For example, if the second injection has taken place, the bands forming due to this second injection will gradually form in between the bands of the first injection. This rising profile can be very useful. Alternatively, imaging could take place once the bands from the second injection have fully formed and then a comparison could be made with the previous separation pattern where only one injection was in the channel. However, the rising profiles can be a very useful tool to remove systematic errors in the imaging and quantitation of a given band. For example, by plotting signal strength versus time for a given band, a more reliable measurement of the true size of the signal could be obtained.

The method of sequential injection of various samples, can be used as a tool to design separation protocols of complex or multiple samples. Chemical reactions between the sample components or between the components and the buffer can be taken into account in consideration for the order of injection. In addition other parameters like the temperature, varying buffer pH can be part of the running protocol. Bands can be extracted from one separation channel and transported to another where different chemical or environmental conditions apply. Additional molecules can be injected externally and sequentially into the new separation channel.

In order to assess the expected resolution of the device we use the experimentally measured mobilities of DNA bands in standard capillary electrophoresis in linear polyacrylamide gels and apply the Lamm equation to derive the expected resolution for the proposed invention. A detailed analysis will not be provided here, but the technique allows a comparison of the expected resolution with that achieved by conventional techniques.

Figure 29A:
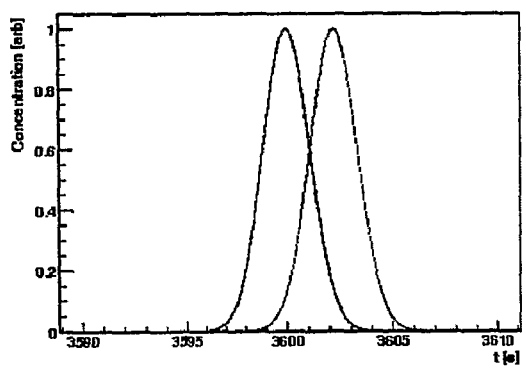
FIGS. 29a, b and c are graphs depicting two DNA bands separated under conventional capillary electrophoresis conditions.
Figure 29B:
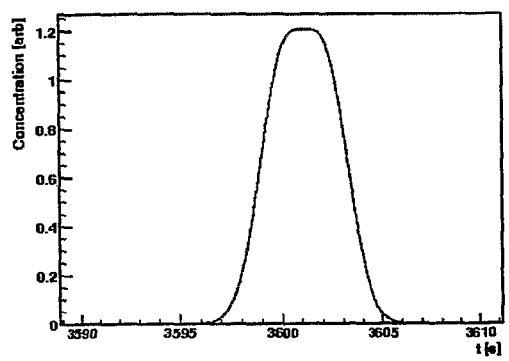
Figure 29C:
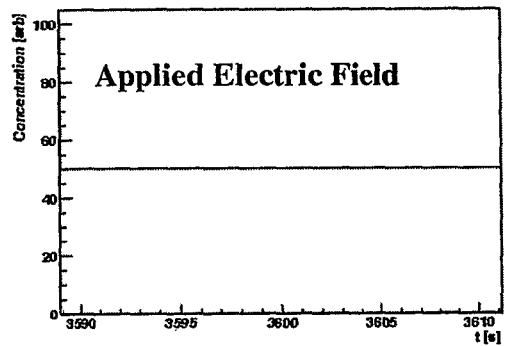

We have studied the mobility of DNA in standard capilliary gel electrophoresis (CGE) from the literature. The conditions assume 6% linear Polyacrylamide gel and a time dependent electric field. FIGS. 29$a$ to $c$ show the expected resolution of a standard CGE experiment with two DNA bands, one 1000 bp and one 1001 bp long. FIG. 29$a$ shows the expected band shapes (bell-shaped) at the detection point (30 cm separation length). As we can see the bands are very close. FIG. 29$b$ shows the sum of the two signals and in this case the sum barely shows the existence of two distinct bands. This is what is expected for this length of DNA and known resolution for CGE separation of DNA in Polyacrylamide gels.

Figure 30A:
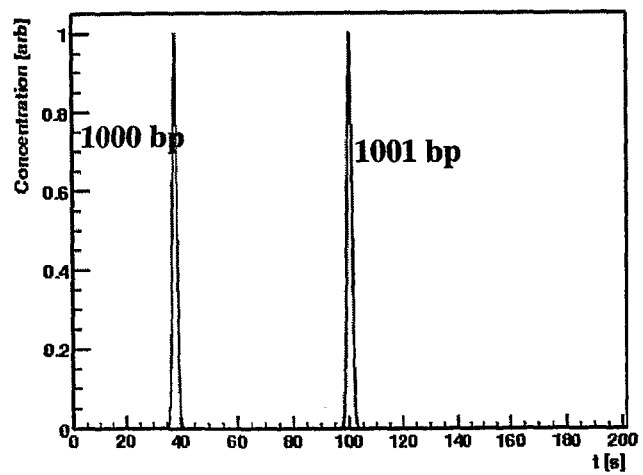
FIGS. 30a, b and c are graphs depicting two DNA bands separated under similar conditions using a device as herein disclosed.
Figure 30B:
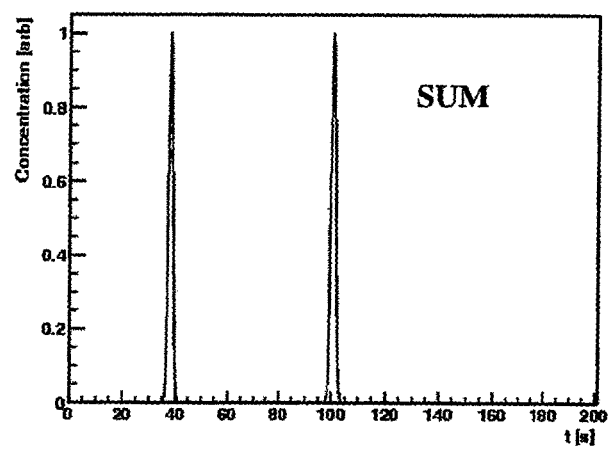
Figure 30C:
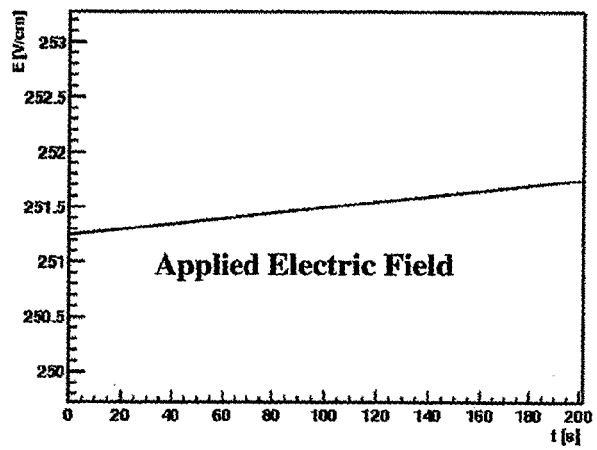

We can predict the resolution of the device herein disclosed for the same DNA bands (1000+1001 bp). FIG. 30$a$ shows the two bands. It is clear that in units of FWHM they are further apart compared to standard CGE (FIGS. 29$a$ to $c$). FIG. 30$b$ shows the sum of the two signals which are clearly resolved and FIG. 30$c$ shows the time-dependent electric field which is at about 250 V/cm. This value is very realistic for such gels. For standard CGE the optimal value is below 50V/cm to achieve the best resolution. Higher electric fields cause decrease of the resolution because for various reasons the dispersion of the DNA bands increases. However for the proposed device, the same rule does not apply since the dispersion is contained by the special separation conditions. Therefore it is perfectly reasonable to increase the resolution by applying higher fields.

Figure 31A:
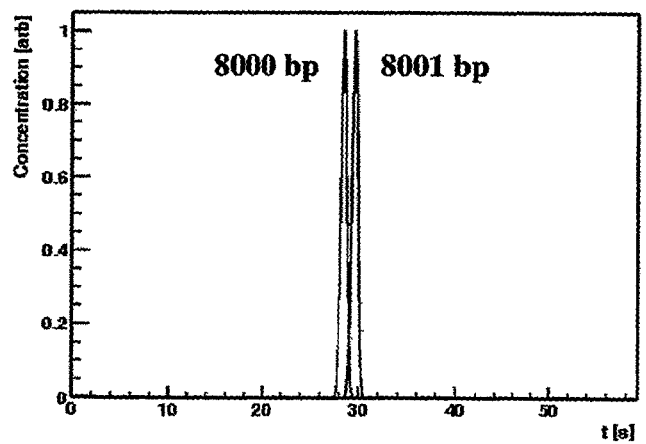
FIGS. 31a, b and c depict two DNA bands, representing longer molecules, separated under similar conditions using a device as herein disclosed.
Figure 31B:
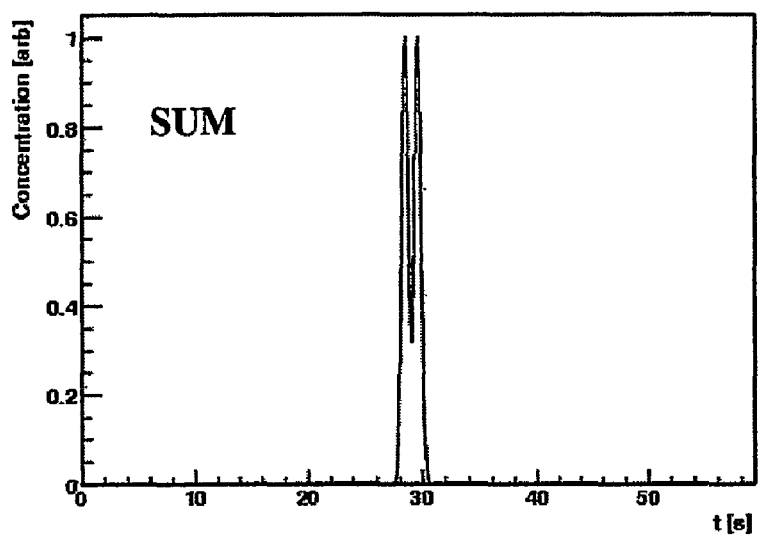
Figure 31C:
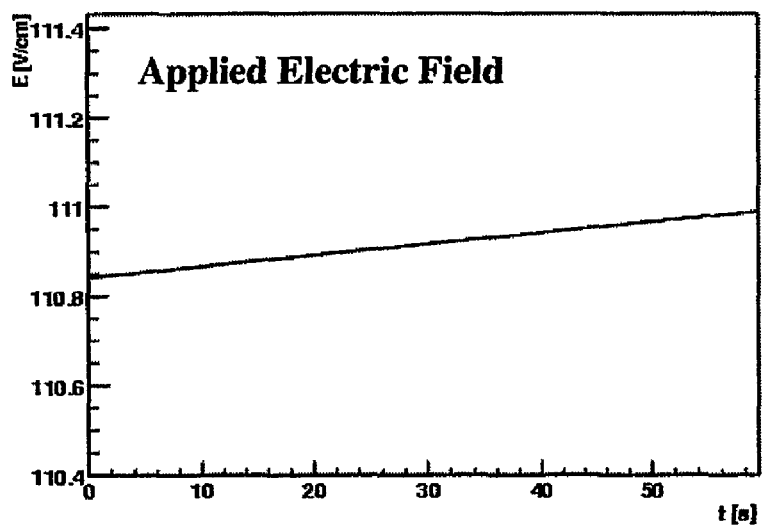

We have used the same data for two longer DNA fragments at 8000 & 8001 bp. FIG. 31$a$ shows the predicted resolution. The two bands are clearly resolved which means that the proposed device would be able to resolve up to an unprecedented resolution of >8000 base pairs of DNA having huge implications for the industry and research.

For a given separation channel, the resolution can be optimised for a given range of friction-charge parameters. In practical terms this would mean for DNA for example that in one channel the "a" parameter of the field can be lowered. The effect of this is that the slope of the field gradient in x reduces but the actual width of the bands does not increase proportionally. This in turn causes the bands in the given dynamic range to move further apart from each other but the band widening does not cancel out the increase in distance. This means that effectively the resolution is increased and since a can be reduced, the resolution for a given dynamic range can be adjusted easily. The reason for this is because in the Lamm analysis, the term that contains f depends linearly on x but the term that contains a depends on $x_2$. However f is inversely proportional to the diffusion coefficient D and therefore the width of a given band. Because of this differential dependence off and a on x the resolution can be effectively adjusted.

One additional useful factor for adjusting the resolution is the parameter k. By increasing this factor the resolution increases dramatically. However this comes at a cost. The electric field range where the separation occurs increases with k and therefore there is a limitation of how large an electric field one can realistically generate in the separation channel for a given HV supply (cost) and voltage-breakdown characteristics of the dielectric of the chip material.

While certain embodiments of the present invention have been described, it will be appreciated that changes and modifications can be made and that other embodiments may be devised without departing from the true spirit and scope of the invention.

What is claimed is:

1. An electrophoresis method for separating objects in a fluid contained in a separation channel, the method comprising:
   applying an electric field along the separation channel, the electric field having a field profile whereby the magnitude of the electric field varies spatially along at least a portion of the separation channel, and thereby causing at least some of the objects to move relative to the fluid;
   varying the applied electric field so as to adjust the field profile relative to the separation channel, thereby causing the objects to separate into bands according to the objects electrical and hydrodynamic properties under the combined influences of an electric force due to the electric field and a hydrodynamic force due to the fluid, each band comprising objects with like electrical and hydrodynamic properties;

wherein the electric field profile is shaped such that the net force experienced by each object, resulting from the combination of the electric force exerted by the field and the hydrodynamic force exerted by the fluid, is such that the width of each separated band remains substantially constant with time; and wherein the fluid and the separation channel are substantially stationary with respect to one another.

2. An electrophoresis method for separating objects according to claim 1 wherein at least a portion of the electric field profile has a gradient which is non-zero.

3. An electrophoresis method for separating objects according to claim 1 wherein the electric field is varied in such a way that the field profile moves relative to the separation channel.

4. An electrophoresis method for separating objects according to claim 3 wherein the field profile remains otherwise unchanged as it moves relative to the separation channel.

5. An electrophoresis method for separating objects according to claim 1 wherein the electric field is varied in such a way that the electric field profile translates along the separation channel.

6. An electrophoresis method for separating objects according to claim 1 wherein the applied electric field is varied such that, once the objects have separated into bands, each band moves with a non-zero terminal velocity relative to the separation channel.

7. An electrophoresis method for separating objects according to claim 6 wherein the terminal velocity of each band is substantially the same.

8. An electrophoresis method for separating objects according to claim 1 wherein the applied electric field is of the form $$E(x,t)=E((x-kt)^n)$$

where x is a space coordinate, typically along the separation channel, t is a time coordinate, n and k are each real numbers and n is not zero.

9. An electrophoresis method for separating objects according to claim 1 wherein at least a portion of the electric field is monotonic with respect to distance along the channel.

10. An electrophoresis method for separating objects according to claim 1 further comprising the steps of mixing the objects to be separated with the fluid and placing the mixture in the separation channel.

11. An electrophoresis method for separating objects according to claim 1, further comprising the steps of placing the fluid in the separation channel and inserting a sample into the separation channel, the sample comprising at least objects to be separated.

12. An electrophoresis method for separating objects according to claim 11 wherein the sample further comprises fluid.

13. An electrophoresis method for separating objects according to claim 1, further comprising the step of detecting the bands.

14. An electrophoresis method for separating objects according to claim 1, further comprising the step of modifying the electric field, after the objects have separated into bands, to adjust spacing between the bands, band positioning or band resolution.

15. An electrophoresis method for separating objects according to claim 14 wherein the electric field is modified by change to its time-dependence and/or its intensity.

16. An electrophoresis method for separating objects according to claim 1, further comprising the step of extracting a band of interest from the separation channel after the objects have separated.

17. An electrophoresis method for separating objects according to claim 1, further comprising the step of oscillating the electric field, causing the motion of the bands to reverse in direction, the bands thus moving back and forth along the separation channel.

18. An electrophoresis method for separating objects according to claim 1, wherein the separation channel is a closed loop and the applied electric field is periodic around the loop.

19. An electrophoresis method for separating objects according to claim 1 wherein the electric field is applied by means of a plurality of electrodes disposed along the separation channel.

20. An electrophoresis method according to claim 19 wherein at least some of the plurality of electrodes are spaced from the interior of the separation channel by a layer of electrically resistive material.

21. An electrophoresis method according to claim 20 wherein the electrically resistive material is a semiconductor.

22. An electrophoresis method according to claim 21 wherein the semiconductor is a doped semiconductor.

23. An electrophoresis method according to claim 22 wherein the electrically resistive material is doped silicon.

24. An electrophoresis method for separating objects according to claim 19 wherein the plurality of electrodes are spaced from the interior of the separation channel such that current is not conducted between the electrodes and the fluid.

25. An electrophoresis method for separating objects according to claim 1 wherein the objects to be separated comprise biomolecules, proteins, polymers, DNA, RNA or biological cells.

26. An electrophoresis device for separating objects, the device comprising:

a separation channel which, in use, contains a fluid and the objects to be separated;

means for applying an electric field along the separation channel, the electric field having a field profile whereby the magnitude of the electronic field varies spatially along at least a portion of the separation channel, such that in use, objects in the separation channel are caused to move relative to the fluid;

a controller adapted in use to apply and vary the applied electric field so as to adjust the electric field profile relative to the separation channel, whereby objects in the separation channel are caused to separate into bands according to the objects' electrical and hydrodynamic properties under the combined influences of an electric force due to the electric field and a hydrodynamic force due to the fluid; each band comprising objects with like electrical and hydrodynamic properties;

wherein the controller is further adapted to apply an electric field profile shaped such that the net force experienced by each object, resulting from the combination of the electric force exerted by the field and the hydrodynamic force exerted by the fluid, is such that each separated band undergoes substantially zero spatial diffusion; and wherein in use, the fluid contained in the separation channel is substantially stationary relative to the separation channel.

27. An electrophoresis device for separating objects according to claim 26 where at least a portion of the electric field profile has a gradient which is non-zero.

28. An electrophoresis device for separating objects according to claim 26 wherein the controller is further adapted to move the electric field profile relative to the separation channel.

29. An electrophoresis device for separating objects according to claim 28 wherein the controller is further adapted to keep the field profile unchanged as it moves relative to the separation channel.

30. An electrophoresis device for separating objects according to claim 28 wherein the controller is further adapted to translate the electric field profile along the separation channel.

31. An electrophoresis device for separating objects according to claim 26 wherein the controller is further adapted to vary the applied electric field such that, once the objects have separated into bands, each band moves with a non-zero terminal velocity relative to the separation channel.

32. An electrophoresis device for separating objects according to claim 31 wherein the terminal velocity of each band is substantially the same.

33. An electrophoresis device for separating objects according to claim 26 wherein the applied electric field is of the form $$E(x,t)=E((x-kt)^n)$$

where x is a space coordinate typically along the separation channel, t is a time coordinate, n and k are each real numbers and n is not zero.

34. An electrophoresis device for separating objects according to claim 26 wherein at least a portion of the electric field is monotonic with respect to distance along the channel.

35. An electrophoresis device for separating objects according to claim 26 wherein the means for applying an electric field comprise a plurality of electrodes disposed along the separation channel.

36. An electrophoresis device for separating objects according to claim 35 wherein at least some of the plurality of electrodes are spaced from the interior of the separation channel by a layer of electrically resistive material.

37. An electrophoresis device for separating objects according to claim 36 wherein the electrically resistive material is a semiconductor.

38. An electrophoresis device for separating objects according to claim 37 wherein the semiconductor is a doped semiconductor.

39. An electrophoresis device for separating objects according to claim 38 wherein the resistive material is doped silicon.

40. An electrophoresis device for separating objects according to claim 35 wherein the electrodes are spaced from the interior of the separation channel such that current is not conducted between the electrodes and the fluid.

41. An electrophoresis device for separating objects according to claim 35 wherein the electrodes comprise conductive ink printed on or adjacent to the separation channel or resistive material.

42. An electrophoresis device for separating objects according to claim 26 wherein the separation channel is a capillary.

43. An electrophoresis device for separating objects according to claim 26 wherein the separation channel is rectilinear.

44. An electrophoresis device for separating objects according to claim 26 wherein the separation channel is in the form of a closed loop.

45. An electrophoresis device for separating objects according to claim 44 wherein the separation channel is circular.

46. An electrophoresis device for separating objects according to claim 26 wherein the separation channel is engraved in a substrate.

47. An electrophoresis device for separating objects according to claim 26 wherein the device is a microfluidic device.

48. An electrophoresis device for separating objects according to claim 26, further comprising a detector adapted to detect bands in the separation channel.

49. An electrophoresis device for separating objects according to claim 48 wherein the detector is adapted to image bands in the separation channel.

50. An electrophoresis device for separating objects according to claim 26 wherein the separation channel is provided with at least one input port for insertion of a sample into the separation channel, the sample comprising at least objects to be separated.

51. An electrophoresis device for separating objects according to claim 26 wherein the separation channel is provided with at least one exit port for extraction of bands of objects from the separation channel.

52. An electrophoresis device for separating objects according to claim 26 comprising a plurality of separation channels, each separation channel being provided with means for applying an electric field and a controller.

53. An electrophoresis device for separating objects according to claim 52 wherein the electric field applied to each separation channel is the same.

54. An electrophoresis device for separating objects according to claim 52 wherein the electric field applied to each separation channel is controlled by the same controller.

* * * * *